(12) United States Patent
Pikul et al.

(10) Patent No.: US 11,617,411 B2
(45) Date of Patent: Apr. 4, 2023

(54) ANTI-INFECTIVE SHOE SOLES

(71) Applicant: Karnali Innovations LLC, Burlington, CO (US)

(72) Inventors: Abbey L. Pikul, Buena Vista, CO (US); Kolby L. Melia, Burlington, CO (US); Mark T. Muller, Buena Vista, CO (US)

(73) Assignee: Karnali Innovations LLC, Burlington, CO (US)

( * ) Notice: Subject to any disclaimer, the term of this patent is extended or adjusted under 35 U.S.C. 154(b) by 206 days.

(21) Appl. No.: 16/899,032

(22) Filed: Jun. 11, 2020

(65) Prior Publication Data

US 2020/0390187 A1 Dec. 17, 2020

Related U.S. Application Data

(60) Provisional application No. 63/009,441, filed on Apr. 13, 2020, provisional application No. 62/859,917, filed on Jun. 11, 2019.

(51) Int. Cl.
| | |
|---|---|
| *A43B 13/10* | (2006.01) |
| *A43B 7/00* | (2006.01) |
| *A43B 13/14* | (2006.01) |
| *A43B 13/04* | (2006.01) |
| *A61L 2/238* | (2006.01) |
| *A01N 59/20* | (2006.01) |
| *A01N 25/34* | (2006.01) |
| *A43B 5/00* | (2022.01) |

(52) U.S. Cl.
CPC .............. *A43B 13/10* (2013.01); *A01N 25/34* (2013.01); *A01N 59/20* (2013.01); *A43B 7/00* (2013.01); *A43B 13/04* (2013.01); *A43B 13/14* (2013.01); *A43B 13/141* (2013.01); *A61L 2/238* (2013.01); *A43B 5/00* (2013.01)

(58) Field of Classification Search
None
See application file for complete search history.

(56) References Cited

U.S. PATENT DOCUMENTS

| | | | | |
|---|---|---|---|---|
| 4,015,347 A | * | 4/1977 | Morishita | A43B 17/04 36/44 |
| 4,151,660 A | * | 5/1979 | Yoshimi | A43B 17/04 36/44 |
| 4,703,754 A | * | 11/1987 | Ibbott | A43B 3/34 429/127 |

(Continued)

FOREIGN PATENT DOCUMENTS

| | | |
|---|---|---|
| CN | 201101177 | 8/2008 |
| CN | 102850632 | 1/2013 |

(Continued)

OTHER PUBLICATIONS

Boyce, "Environmental contamination makes an important contribution to hospital infection," J. Hosp. Infect., 65:50-54, 2007.

(Continued)

*Primary Examiner* — Jila M Mohandesi
(74) *Attorney, Agent, or Firm* — Fish & Richardson P.C.

(57) ABSTRACT

Shoe outsoles having anti-infective properties are provided herein, as are methods and materials for making shoes and shoe outsoles having anti-infective properties.

21 Claims, 21 Drawing Sheets

(56) References Cited

U.S. PATENT DOCUMENTS

| | | | | |
|---|---|---|---|---|
| 7,516,506 | B2* | 4/2009 | Koo | A43B 13/12 12/146 B |
| 7,713,457 | B2* | 5/2010 | Koo | B29C 43/305 264/172.19 |
| 8,661,713 | B2* | 3/2014 | Koo | A43B 13/122 36/8.1 |
| 8,914,995 | B2* | 12/2014 | Andrews | A43B 7/144 36/152 |
| 9,078,492 | B2* | 7/2015 | Koo | A43B 13/02 |
| 10,143,267 | B1* | 12/2018 | Koo | A43B 13/22 |
| 2003/0170453 | A1 | 9/2003 | Foss et al. | |
| 2007/0017124 | A1* | 1/2007 | Koo | A43B 13/12 36/59 C |
| 2014/0096414 | A1* | 4/2014 | Koo | B29C 43/28 36/103 |
| 2019/0218710 | A1* | 7/2019 | Chang | D02G 3/449 |
| 2021/0299310 | A1* | 9/2021 | Smith | B32B 15/14 |
| 2022/0087344 | A1* | 3/2022 | Gueritee | A41D 1/002 |
| 2022/0087365 | A1* | 3/2022 | Cooper | A43B 23/027 |

FOREIGN PATENT DOCUMENTS

| | | |
|---|---|---|
| CN | 107440213 | 12/2017 |
| JP | 2006-254931 | 9/2006 |
| JP | 2014057619 | 4/2014 |
| KR | 20-0278139 | 6/2002 |
| KR | 10-2012-0128489 | 11/2012 |
| TW | 696716 B1 * | 6/2020 |

OTHER PUBLICATIONS

Casey et al., "Role of copper in reducing hospital environment contamination," J. Hosp. Infect., 74:72-77, 2010.

Elguindi et al., "Genes involved in copper resistance influence survival of *Pseudomonas aeruginosa* on copper surfaces," J. Appl. Microbiol., 106:1448-1455, 2009.

Gould et al., "The antimicrobial properties of copper surfaces against a range of important nosocomial pathogens," Ann. Microbiol., 59:151-156, 2009.

Inkinen et al., "Diversity of ribosomal 16S DNA- and RNA-based bacterial community in an office building drinking water system," Lett. Appl. Microbiol., 64:19-26, 2016.

Karpanen et al., "The antimicrobial efficacy of copper alloy furnishing in the clinical environment: a crossover study," Infect. Control Hosp. Epidemiol., 33:3-9, 2012.

Koseoglu Eser et al., "Antimicrobial activity of copper alloys against invasive multidrug-resistant nosocomial pathogens," Curr. Microbiol., 71:291-295, 2015.

Mehtar et al., "The antimicrobial activity of copper and copper alloys against nosocomial pathogens and *Mycobacterium tuberculosis* isolated from healthcare facilities in the Western Cape: an in-vitro study," J. Hosp. Infect., 68:45-51, 2008.

Michels et al., "Effects of temperature and humidity on the efficacy of methicillin-resistant *Staphylococcus aureus* challenged antimicrobial materials containing silver and copper," Lett. Appl. Microbiol., 49:191-195, 2009.

Mikolay et al., "Survival of bacteria on metallic copper surfaces in a hospital trial," Appl. Microbiol. Biotechnol., 87:1875-1879, 2010.

Noyce et al., "Potential use of copper surfaces to reduce survival of epidemic meticillin-resistant *Staphylococcus aureus* in the healthcare environment," J. Hosp. Infect., 63:289-297, 2006.

Otter et al., "Evidence that contaminated surfaces contribute to the transmission of hospital pathogens and an overview of strategies to address contaminated surfaces in hospital settings," Am. J. Infect. Control, 41:S6-S11, 2013.

Schmidt et al., "Sustained reduction of microbial burden on common hospital surfaces through introduction of copper," J. Clin. Microbiol., 50:2217-2223, 2012.

Van Doremalen et al., Aerosol and surface stability of SARS-CoV-2 as compared with SARS-CoV-1, New Engl. J. Med., Letter to the Editor, 2020, pp. 1-3.

Wilks et al., "The survival of *E. coli* O157 on a range of metal surfaces," Int. J. Food Microbiol., 105:445-454, 2005.

International Preliminary Report on Patentability in International Appln. No. PCT/US2020/037245, dated Dec. 23, 2021, 7 pages.

PCT International Search Report and Written Opinion in International Appln. No. PCT/US2020/037245, dated Sep. 30, 2020, 8 pages.

* cited by examiner

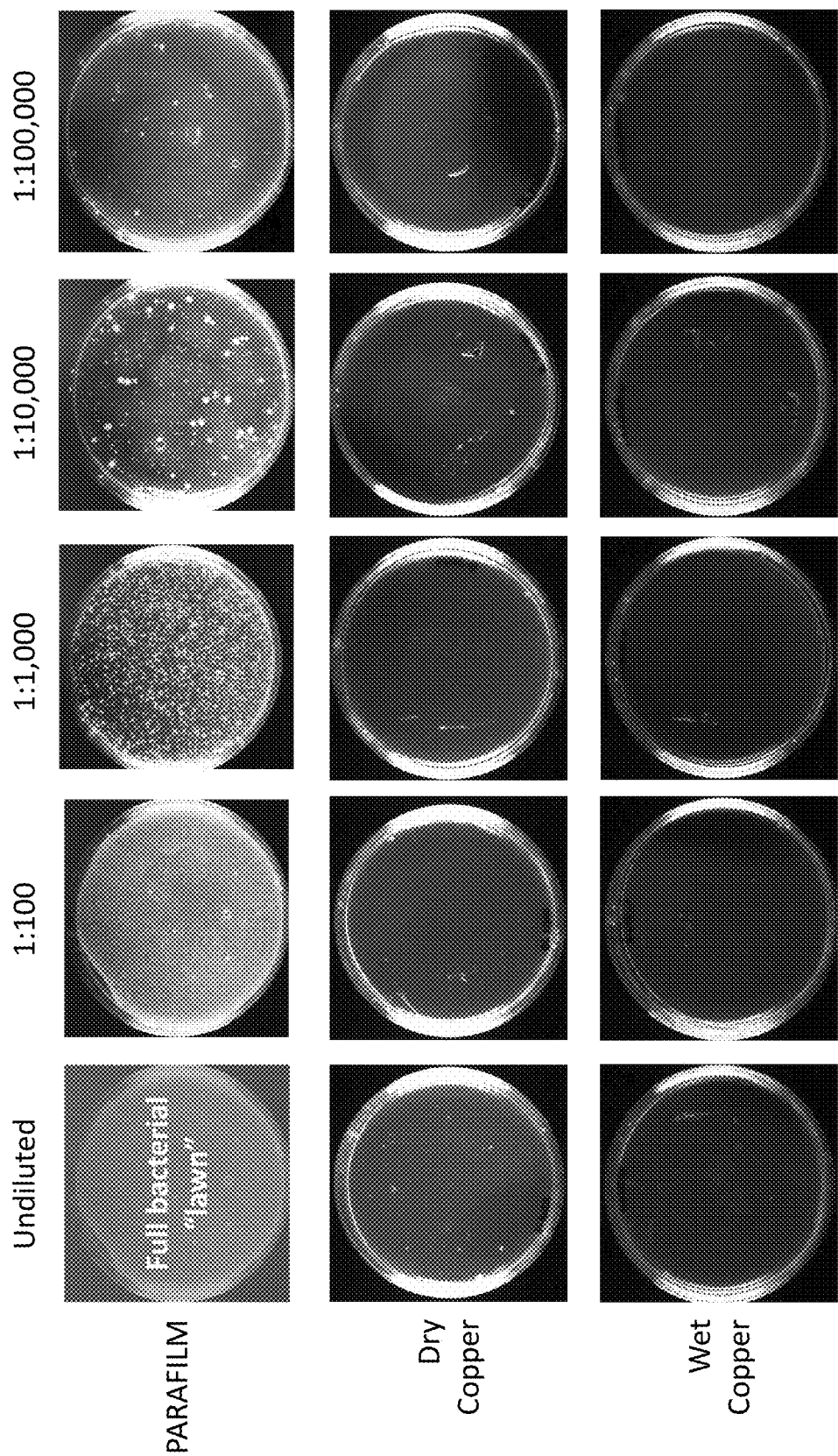

ANTI-INFECTIVE SHOE SOLES

CROSS-REFERENCE TO RELATED APPLICATIONS

This application claims benefit of priority from U.S. Provisional Application No. 63/009,441, filed on Apr. 13, 2020, and U.S. Provisional Application No. 62/859,917, filed on Jun. 11, 2019.

TECHNICAL FIELD

This document relates to shoe soles (e.g., shoe outsoles) that have anti-infective properties, and to methods and materials for making shoes and shoe soles (e.g., outsoles) having anti-infective properties.

BACKGROUND

Shoes and shoe parts, including outsoles, can have a role in colonization and transmission of pathogens such as bacteria and viruses from one location to another. In some cases, shoes can act as vectors for transmission of potentially harmful infectious agents (e.g., bacteria, fungi, and viruses) into new environments, and can transfer the infections agents to human or animal hosts that have the potential for infection. The transfer of such infectious agents from one location (e.g., a higher risk environment such as a hospital) to a home or other site, particularly where there are people who are immunocompromised or otherwise at increased risk of infection, can be especially problematic. This is classic cross-contamination, and is an acute problem not only in healthcare, but also in the spread of disease globally.

SUMMARY

This document is based, at least in part, on the development of novel outsoles for use with any type of footwear, where the outsoles have anti-infective properties that effectively mitigate cross-contamination by killing or inactivating pathogens such as bacteria, fungi, and viruses. Without being bound by a particular mechanism, the outsoles described herein can utilize the oligodynamic effect, in which metals (e.g., heavy metals) have a biocidal effect on bacterial microorganisms and viruses. The outsoles can include, for example, particles of metal dispersed throughout the outsole material, or pieces of metal at discrete locations within and/or on the outsole. When an infective agent (e.g., an infectious virus particle or a pathogenic eukaryotic or prokaryotic microbe, such as a bacterium, fungus, or yeast) comes into contact with the metal, the infective agent is inactivated or killed, and therefore is rendered non-infectious or less infectious even if it is transferred to a new location or if it comes into contact with a human or animal host.

In a first aspect, this document features a sole structure for an article of footwear, where the sole structure includes a member defining a foot-supporting surface and a ground-facing surface, the ground-facing surface having ground contacting regions and non-ground contacting regions, where one or more of the non-ground contacting regions includes an anti-infective agent. The anti-infective agent can be effective to inactivate or kill pathogenic biological agents disposed on the sole structure. The pathogenic biological agents can be selected from the group consisting of bacteria, viruses, fungi, and yeast. The anti-infective agent can be effective to inactivate or kill from about 50% to about 99% of the pathogenic biological agents. The anti-infective agent can be effective to inactivate or kill the pathogenic biological agents within about 5 minutes to about 24 hours. Two or more of the non-ground contacting regions can include a discrete area incorporating the anti-infective agent, where each discrete area is generally spaced apart from a nearest neighboring discrete area by no more than a predetermined distance (e.g., from about 0.1 mm to about 50 mm). The ground-facing surface can have a plurality of projections, where the ground contacting regions are defined by a distal most predetermined height of the projections, and where the non-ground contacting regions are defined by surfaces of the projections at heights that are less than the distal most predetermined height. The anti-infective agent can include a metallic material. The metallic material can include copper, a copper alloy, a coordinated copper complex, a copper-containing compound, or a copper chelate. The sole can be an outsole or a midsole. The member can include a flexible material (e.g., a polymer selected from the group consisting of natural rubber, a vulcanized rubber, polyurethane, and silicone).

In another aspect, this document features a sole structure for an article of footwear, where the sole structure includes a member having a first end and a second end that is opposite the first end in a longitudinal direction, where the member defines a foot-supporting surface and a ground-facing surface, and where the member includes a polymer and an anti-infective agent dispersed throughout the polymer. The anti-infective agent can be effective to inactivate or kill pathogenic biological agents disposed on the sole structure. The pathogenic biological agents can be selected from the group consisting of bacteria, viruses, fungi, and yeast. The anti-infective agent can include a metallic material. The metallic material can include copper, a copper alloy, a coordinated copper complex, a copper-containing compound, or a copper chelate. The member can be an outsole or a midsole. The polymer can be selected from the group consisting of natural rubber, a vulcanized rubber, polyurethane, and silicone. The anti-infective agent can include a plurality of irregularly-shaped particles.

In another aspect, this document features an article of footwear having an upper and a sole structure engaged with the upper, where the sole structure includes a member having a first end portion and a second end portion that is opposite the first end in a longitudinal direction, where the member defines a foot-supporting surface and a ground-facing surface, where the ground-facing surface includes ground contacting regions and non-ground contacting regions, and where one or more of the non-ground contacting regions includes an anti-infective agent. The member can be a coupleable member that attaches to an outsole fixedly attached to the upper. The member can be an outsole or can be fixedly attached to the outsole. The non-ground contacting region can be located at the first end portion, the second end portion, a mid-portion located between the first end portion and the second end portion, or combinations thereof, where the first end portion is a toe location of the article of footwear, and where the second end portion is a heel location of the article of the footwear.

In another aspect, this document features a sole structure for an article of footwear. The sole structure can include a member having a first end and a second end that is opposite the first end in a longitudinal direction, the member defining a foot-supporting surface and a ground-facing surface, the ground-facing surface having ground contacting regions and non-ground contacting regions, where one or more of the non-ground contacting regions includes an anti-infective agent. The anti-infective agent can be effective to inactivate or kill pathogenic biological agents (e.g., bacteria, viruses, fungi, or yeast) that make surface contact with the sole structure. Two or more of the non-ground contacting regions can include a discrete area incorporating the anti-infective agent, where each discrete area is generally spaced apart from a nearest neighboring discrete area by no more than a predetermined distance. The predetermined distance can be from 0.1 mm to 50 mm, from about 1 mm to about 40 mm, from about 5 mm to about 30 mm, from about 10 mm to about 25 mm, from about 5 mm to about 10 mm, from about 10 mm to about 40 mm, or from about 1 mm to about 10 mm. The ground-facing surface can include a plurality of projections or treads, where the ground contacting regions are defined by a distal most predetermined height of the projections, and where the non-ground contacting regions are defined by surfaces of the projections at heights that are less than the distal most predetermined height. The anti-infective agent can include a metallic material. The metallic material can include a metal, a metal salt, a metal compound, a metal chelate, or a metal alloy. The metallic material can be selected from the group consisting of copper, silver, gold, platinum, palladium, combinations thereof, and alloys thereof. For example, the metallic material can include copper, a copper alloy, a coordinated copper complex, a copper-containing chemical structure, or a copper chelate. The sole can be an outsole or a midsole. The member can include a flexible material. The member can include a polymer (e.g., natural rubber, a vulcanized rubber, polyurethane, or silicone). In some cases, for example, the polymer can include natural rubber or a vulcanized rubber.

In another aspect, this document features a sole structure for an article of footwear, where the sole structure includes a member having a first end and a second end that is opposite the first end in a longitudinal direction, the member defining a foot-supporting surface and a ground-facing surface, and where the member includes a polymer and an anti-infective agent dispersed throughout the polymer. The anti-infective agent can be effective to inactivate or kill pathogenic biological agents (e.g., bacteria, viruses, fungi, or yeast) that come into surface contact with the sole structure. The anti-infective agent can include a metallic material. The metallic material can include a metal, a metal salt, a metal compound, a metal chelate, or a metal alloy. The metallic material can be selected from the group consisting of copper, silver, gold, platinum, palladium, combinations thereof, and alloys thereof. For example, in some cases, the metallic material can include copper, a copper alloy, a coordinated copper complex, a copper-containing chemical structure, or a copper chelate (e.g., particles of copper, a copper alloy, a coordinated copper complex, a copper-containing chemical structure, or a copper chelate). The member can be an outsole or a midsole. The polymer can be selected from the group consisting of natural rubber, a vulcanized rubber, polyurethane, and silicone. In some cases, for example, the polymer can include natural rubber or a vulcanized rubber.

In another aspect, this document features a shoe sole. The shoe sole can include a member having a first end and a second end, the first end being opposite the second end in a longitudinal direction, the member having a first surface attachable to a shoe component, an intermediate surface, and a plurality of projections extending from the intermediate surface in a transverse direction, each projection having a distal most predetermined height, the distal most predetermined heights of the plurality of projections together defining a distal surface of the sole, and each projection having surfaces at heights that are less than the distal most predetermined height, the surfaces defining proximal surfaces of the sole, where the proximal surfaces include an anti-infective agent. The anti-infective agent can be effective to inactivate or kill pathogenic biological agents (e.g., bacteria, viruses, fungi, or yeast) that come into contact with the shoe sole. The anti-infective agent can include a metallic material. The metallic material can include a metal, a metal salt, a metal compound, a metal chelate, or a metal alloy. The metallic material can be selected from the group consisting of copper, silver, gold, platinum, palladium, combinations thereof, and alloys thereof. In some cases, for example, the metallic material can include copper, a copper alloy, a coordinated copper complex, a copper-containing chemical structure, or a copper chelate. The shoe sole can be an outsole or a midsole. The member can include a flexible material. The member can include a polymer. The polymer can be selected from the group consisting of a vulcanized rubber, natural rubber, polyurethane, and silicone. In some cases, for example, the polymer can include natural rubber or a vulcanized rubber. The shoe component can include an upper or a midsole.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 19 is a series of images of Petri plates streaked with the indicated dilutions of *E. coli* strain Rosetta cultures that had been incubated on a PARAFILM® "boat" (negative control; top row), dried on a copper "boat" (middle row), or incubated on a copper "boat" without drying (bottom row). The images show the number of colonies resulting from serial dilutions of each culture. Based on the colony counts, the number of viable bacteria per mL were determined.

DETAILED DESCRIPTION

Figure 1:
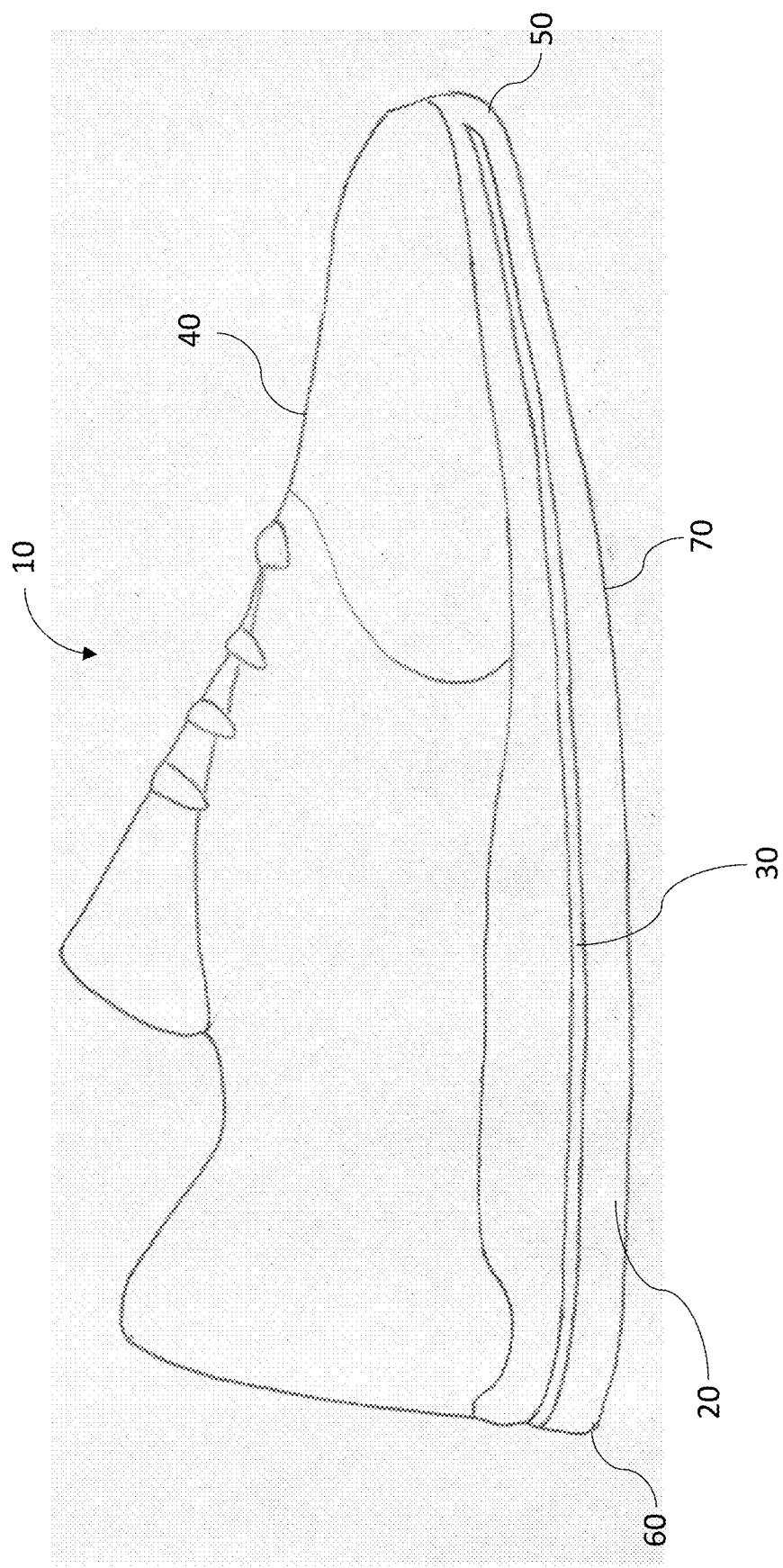
FIG. 1 is an illustration showing the general components of a shoe sole.

Touch surfaces are effective vectors that can foment the spread of pathogenic agents from human to human. Pathogenic bacteria are very hardy and highly evolved free living, single-cell organisms that have adapted to persist on surfaces for days, weeks, or even months (see, Boyce *J Hosp Infect* 65:50-54, 2007; and Otter et al., *Am J Infect Control* 41:S6-S11, 2013). Viruses—including SARS-CoV viruses—also can survive on various surfaces for extended periods of time (van Doremalen et al., *New Engl J Med* 2020, doi 10.1056/NEJMc2004973). Contaminated surfaces can promote pathogenic transmission, particularly in medical settings such as hospitals, emergency rooms, and ambulances, where touch surfaces significantly enhance the risk for acquiring healthcare-associated infections. Other high-risk environments, such as crowded public areas (e.g., schools, offices, and long-term care facilities), also are potential pathogenic or opportunistic transmission zones.

Mitigating this kind of transmission is most effective using multiple layers or barriers for protection, in order to reduce the transmission frequency. Conventional barriers are largely passive in nature, and include proper hand hygiene, air filtration (HEPA filters), swabbing/cleaning practices, sterile attire, hairnets, booties, and comprehensive aseptic technique. While these are all beneficial options, these barriers typically lack an active bactericidal step to actually attack and destroy the pathogen. Passive barriers may still allow direct transmission of bacteria and viruses from contaminated inanimate surfaces to the human body or to other surface sites in another environment, such as the home. This is especially true if the same footwear is worn in the contaminated environment and in the household. Footwear in particular represents an ongoing source of pathogenic spread due to the rather large contact area provided by the sole. In other words, there is continuous contact area between the outer soles of footwear and contaminated surfaces in pathogen-rich, high-risk environments. Creating a sterility barrier to disrupt the cycle of floor to shoe to self-inoculation and transmission, such as continuous scrubbing or flushing with disinfecting agents, is not always practical throughout the work day. In some cases, sterile outer shoe covers (also known as "booties") can be used in high risk areas (e.g., operating rooms or trauma rooms), but booties lose efficacy when exposed to aqueous contaminants, and the spread of pathogens is not effectively blocked by such passive protection. For example, if a pathogen-rich source solution soaks through a shoe cover, there is danger of contamination (e.g., self-inoculation of hands) when removing the outer covers, even with surgical gloves.

Copper is an antibacterial and antiviral material that has been evaluated with pathogens such as *Staphylococcus aureus* (MRSA), enteropathogenic *Escherichia coli*, vancomycin resistant *Enterococcus* species (VRE), yeast (*Candida albicans*), *Klebsiella pneumonia*, *Pseudomonas aeruginosa*, and *Acinetobacter baumannii* (see, e.g., Noyce et al., *J Hosp Infect* 63:289-297, 2006; Mehtar et al., *J Hosp Infect* 68:45-51, 2008; Gould et al., *Ann Microbiol* 59:151-156, 2009; and Koseoglu et al., *Curr Microbiol* 71:291-295, 2015). Bacterial pathogens can be inactivated within minutes to hours depending on inoculation load, ambient temperatures, copper content, relative humidity and water content, and associated proteins (Elguindi et al., *J Appl. Microbiol.* 106:1448-1455, 2009; Michels et al., *Lett. Appl. Microbiol.* 49:191-195, 2009; and Wilks et al., *Int. J. Food Microbiol.* 105:445-454, 2005). Studies in hospitals have shown reduced total microbial counts and a lower occurrence of pathogens (specifically, VRE and MRSA) in the presence of copper surfaces (Casey et al., *J Hosp Infect* 74:72-77, 2010; Mikolay et al., *Appl Microbiol Biotechnol* 87:1875-1879, 2010; Karpanen et al., *Infect Control Hosp Epidemiol* 33:3-9, 2012; and Schmidt et al., *J Clin Microbiol* 50:2217-2223, 2012). Various facilities and touch surface types, such as door knobs, light switches, and toilet handles, have been studied with different cleaning practices and usage profiles (Inkinen et al., *Lett Appl Microbiol* 64:19-26, 2016). These studies identified touch surface types that possess the highest bacterial loads in facilities in which individuals routinely work, recuperate, or play, and demonstrated the antibacterial efficacy of copper-containing products as functional antimicrobial materials. Studies also showed that the SARS-CoV-1 virus and the SARS-CoV-2 virus (the strain that causes COVID-19) do not survive as long on copper as on other surfaces (van Doremalen et al., supra), and indicated that SARS-CoV-2 is more sensitive to copper than SARS-CoV. Without being bound by a particular mechanism, it is believed that $Cu^{2+}$ ions can induce reactive oxygen species that can target DNA or RNA of infectious agents and mutate or destroy bacterial cells and virus particles.

The methods and materials described herein are based, at least in part, on the discovery that heavy metals (e.g., copper) incorporated into a sole (e.g., an outsole or midsole) for an article of footwear can confer biocidal capabilities to the footwear. Although reference is made throughout this document to "shoe" and "shoes," it is to be noted that the soles described herein can be used with any appropriate type of footwear (e.g., shoes, boots, sandals, and slippers). The methods and materials described herein also are based, at least in part, on the development of methods for producing shoe soles (e.g., outsoles or midsoles) that contain one or more metal components in an amount and configuration sufficient to confer biocidal capabilities to the sole. Thus, this document provides soles (e.g., outsoles) containing a heavy metal component, shoes that include the soles, and methods for making the soles.

The terms "biocidal" and "anti-infective," as used herein, refer to the ability of an agent (e.g., a metal having anti-infective properties, such as a heavy metal) to lead to the death of infectious pathogens such as bacteria, viruses, and fungi, for example. Any appropriate metal (e.g., heavy metal, which typically has a density of at least 5 $g/cm^3$) or metal alloy can be used as an anti-infective in the soles provided herein. For example, a heavy metal or alloy included in an outsole can be, without limitation, antimony, bismuth, copper, gold, lead, nickel, cupronickel, silver, thallium, tin, brass, zinc, bronze, or any combination thereof. Heavy metals such as mercury and arsenic typically are not used in the outsoles provided herein, as these metals have significant toxicity profiles with the potential to cause harm to humans, animals, and the environment.

In some embodiments, the metal used in the soles and shoes provided herein can be 100% pure, or can be nearly pure (e.g., at least 95% pure, at least 98% pure, at least 99% pure, at least 99.5% pure, or at least 99.9% pure). In some cases, the metal used in the soles and shoes provided herein can be about 50% to about 95% pure (e.g., about 50% to about 75% pure, about 75% to about 85% pure, or about 85% to about 95% pure). In some embodiments, the footwear article or components thereof can include metal alloys (e.g., copper alloys, such as brass or bronze), metal compounds, metal chelates, or metal salts. In some cases, for example, an article of footwear can contain copper, a copper alloy, a copper chelate, a coordinated copper complex, or a copper-containing chemical structure (e.g., a pincer-like complex of Cu(II) based on mesityl, phenyl, and cyclohexyl groups that disrupts RNA replicase complexes, a Cu(II) complex that behaves like bleomycin, or a Cu(II) complex that employs pyrrole-based chelates to stabilize the metal ion).

The metal can be used in various physical forms, including particulates or sheets. In some cases, copper can be particularly useful. As described below, for example, particles of powdered copper, copper flakes, copper coatings, copper mesh, or sheets of copper can be incorporated into shoe soles to confer anti-infective properties. It is noted that some metals, including copper, can oxidize over time (also referred to as anodizing), particularly in an aqueous environment. Even after oxidation, however, the metal can still be effective as an anti-infective. Moreover, friction on the sole that occurs during use, as a result of ambulation, can remove oxidation by "polishing" the metal component.

The soles described herein are suitable for use with any shoe type. In general, shoes include an outsole, a midsole, and an insole to support the foot, in addition to the upper components that surround the sides and top of the foot, or portions thereof. A representative example showing the general components of a shoe sole are illustrated in FIG. 1, which depicts a shoe 10 having an outsole 20, a midsole 30, and an upper 40. In some cases, as illustrated in FIG. 1, outsole 10 can have first end 50 and second end 60 that is opposite first end 50 in a longitudinal direction, and also can have a foot-supporting surface (not visible) and ground-facing surface 70. As described herein, one or more metals can be incorporated into the outsole, the midsole, or both, to confer anti-infective properties to the sole.

Shoe soles (e.g., outsoles or midsoles) can have various physical qualities (e.g., flexibility and hardness) and design characteristics (e.g., tread pattern and/or depth), depending on the type of shoe into which the soles are incorporated, or on the purpose for which the shoes will be worn. For example, the soles of athletic shoes typically are more flexible than the soles of work boots or hiking boots. The soles of shoes that are likely to be worn in an environment where traction and stability are important (e.g., for athletes or people who are on their feet much of the time in a hospital or a school setting) typically have deeper treads and/or a more complex tread design. The soles described herein solve the problem of how to incorporate an anti-infective metal into a shoe in order to provide effective contact with infectious agents that transfer from a floor surface to the sole of the shoe (thereby becoming attached to or otherwise disposed on the bottom surface of the shoe), killing the infectious agents and thus reducing their transfer from one environment to another. We should describe examples of "attach to" can include. For example, when a pathogen, or something like this. Yes, it would be good to link this disclosure to how pathogens become trapped in the recesses! Moreover, the soles described herein are designed to retain their anti-infective capabilities even after erosion of the frictional surfaces that typically occurs due to wear. For example, an anti-infective metal can be incorporated into the "valleys" or recesses in the topology of the soles, where pathogens (e.g., bacteria and virus particles) and moisture are likely to become trapped. Trapped biomaterials (e.g., blood, serum, or sputum) are likely to contain an array of pathogenic micro-organisms, and also can promote the viability of carry-over pathogens. The anti-infective surfaces described herein can effectively neutralize pathogens lodged inside such biomaterials.

As used herein, the term "effective contact," with regard to an anti-infective metal on or within the sole of a shoe, means that the anti-infective metal can come into contact with pathogens such as bacteria and viruses and reduce the amount of viable pathogens (e.g., bacterial cells or virus particles) by at least 50% (e.g., at least 60%, at least 70%, at least 75%, at least 80%, at least 85%, at least 90%, at least 95%, about 50% to about 75%, about 50% to about 90%, about 50% to about 95%, about 50% to about 99%, about 75% to about 90%, about 75% to about 95%, about 75% to about 99%, about 90% to about 95%, or about 90% to about 99%) within a predetermined time period, such as 48 hours or less (e.g., 24 hours or less, 15 hours or less, 10 hours or less, 8 hours or less, 6 hours or less, 4 hours or less, 3 hours or less, 2 hours or less, 1 hour or less, 30 minutes or less, 20 minutes or less, 10 minutes or less, 5 minutes or less, 5 to 30 minutes, 30 to 60 minutes, 1 to 2 hours, 2 to 4 hours, 4 to 6 hours, 6 to 8 hours, 8 to 12 hours, 12 to 24 hours, 5 minutes to 1 hour, 30 minutes to 2 hours, 1 to 6 hours, or upon contact). It is noted that "contact" is not necessarily limited to immediate physical contact, since metals can kill infectives that are not in immediate contact with the metal atoms. See, e.g., the Example herein and FIGS. 14, 15A, and 15B, which describe and show the zone of clearing beyond the perimeter of a copper disk.

In general, the degree of efficacy of a sole provided herein can depend on the surface area and/or volume of the anti-infective metal provided in the sole, although it is noted that the size and dimension of anti-infective metal on a sole may affect the sole's flexibility (typically quantified as shore hardness) or comfort. For example, a sole having a large amount of its surface area inlaid with metal may be highly effective, but may be more suitable for a less active wearer such as a laboratory technician, a worker in an operation suite, or for those involved in sterile manufacturing. A sole having a lower amount of its surface area inlaid with metal may be moderately effective, but may also have a lower shore hardness level compatible with more active wearers, such as nurses, police, and first responders. As described in the Example below, discrete copper pieces were surprisingly found to be associated with a "kill zone" extending about 5 mm to about 20 mm beyond their perimeters, indicating that a copper inlay would be effective to kill infectives within at least 5 mm of its surface area. Thus, in some embodiments, the soles provided herein include a plurality of discrete anti-infective surface areas that are spaced apart from a nearest neighboring anti-infective surface area of a predetermined distance of 50 mm or less (e.g., about 45 mm or less, 40 mm or less, 35 mm or less, 30 mm or less, 25 mm or less, 20 mm or less, 15 mm or less, 10 mm or less, 8 mm or less, 5 mm or less, 4 mm or less, 3 mm or less, 2 mm or less, 1 mm or less, or 0.5 mm or less).

Figure 2:
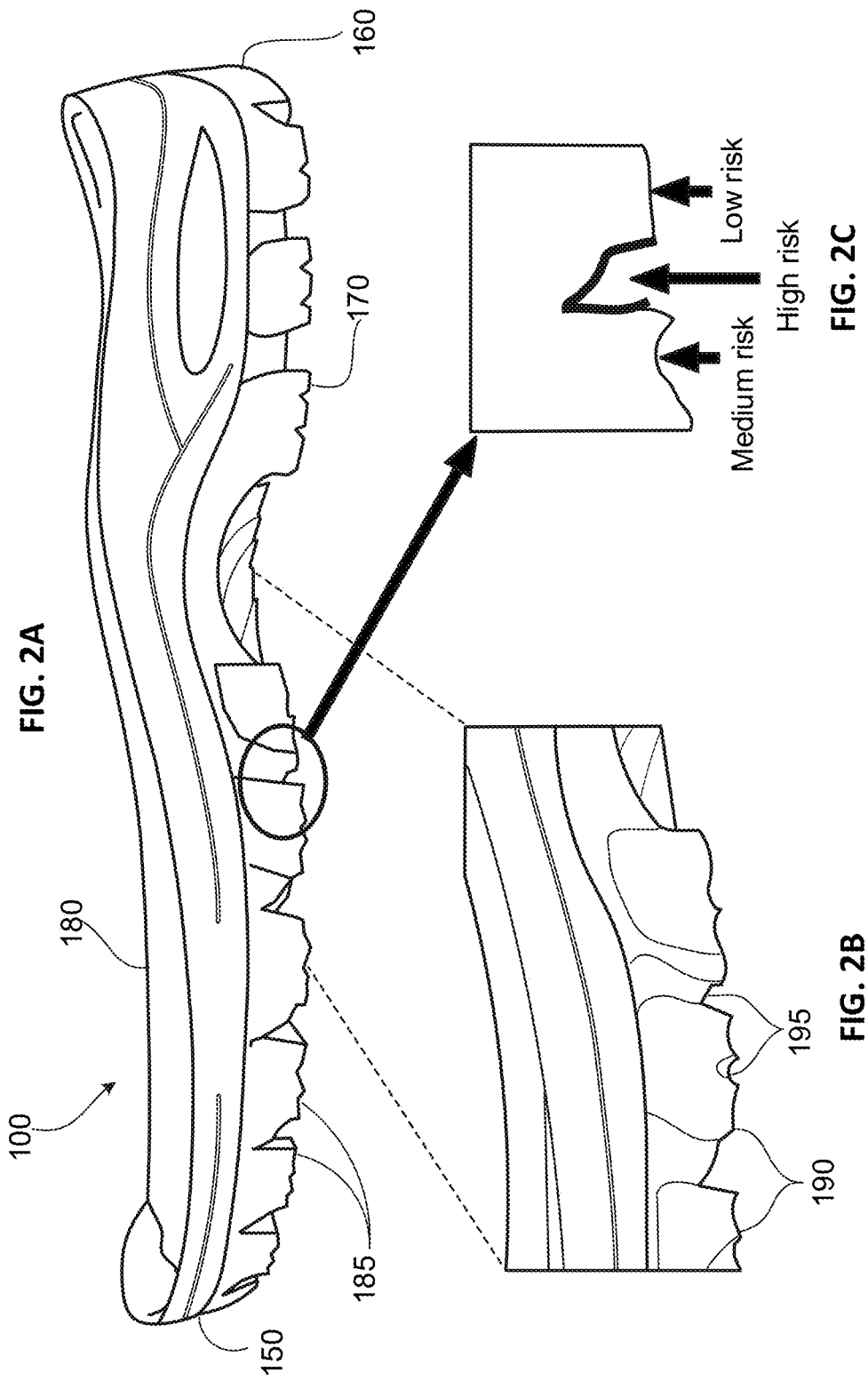
FIG. 2A is a schematic illustrating a shoe sole with treads having recesses of different depths.
FIGS. 2B and 2C show magnified views of the indicated portions of the sole shown in FIG. 2A.

In some cases, in order to provide effective contact with infectives, a metal can be located in areas of highest risk for infective attachment to the sole. Soles that have treads typically have regions of lower, moderate, and higher risk of attachment. A representative example of a sole with treads is shown in FIG. 2A. Sole 100 includes first end 150 and second end 160 that is longitudinally opposite first end 150. Sole 100 also includes ground-facing surface 170 and foot-supporting surface 180, where ground-facing surface 180 defines treads (e.g., treads 185). The treads define recesses of varying depths, which can contribute to the relative risk of infective attachment and transfer. FIGS. 2B and 2C are enlarged views of portions of the sole of FIG. 2A. The treads can have ground-contacting regions 190 and non-ground contacting regions 195 (FIG. 2B). The ground-contacting regions 190 include portions of the ground-facing surface that come into contact with a ground surface during ambulatory use of the footwear product described herein. The non-ground contacting regions 195 include portions of the ground-facing surface that do not come into contact with the ground surface during ambulatory use. As indicated by the arrows in FIG. 2C, for example, the regions of the tread that have the deepest recesses are the regions at highest risk, as such regions are more likely to retain substances (e.g., aqueous solutions, sputum, saliva, feces, blood, serum, and/or sweat) that may be contaminated with infectives such as bacteria and viruses. Recesses that are more shallow still present a risk for retaining contaminants, but the risk is likely to be more moderate. Areas of the tread that do not include a recess are likely to be low risk, since those areas will come into contact with the ground as the wearer walks and will have a high degree of friction, thus removing attached contaminants. Given the above, it can be useful to incorporate a metal (e.g., a heavy metal such as copper) into the areas of a sole that present the greatest risk of retaining contaminants.

Figure 3:
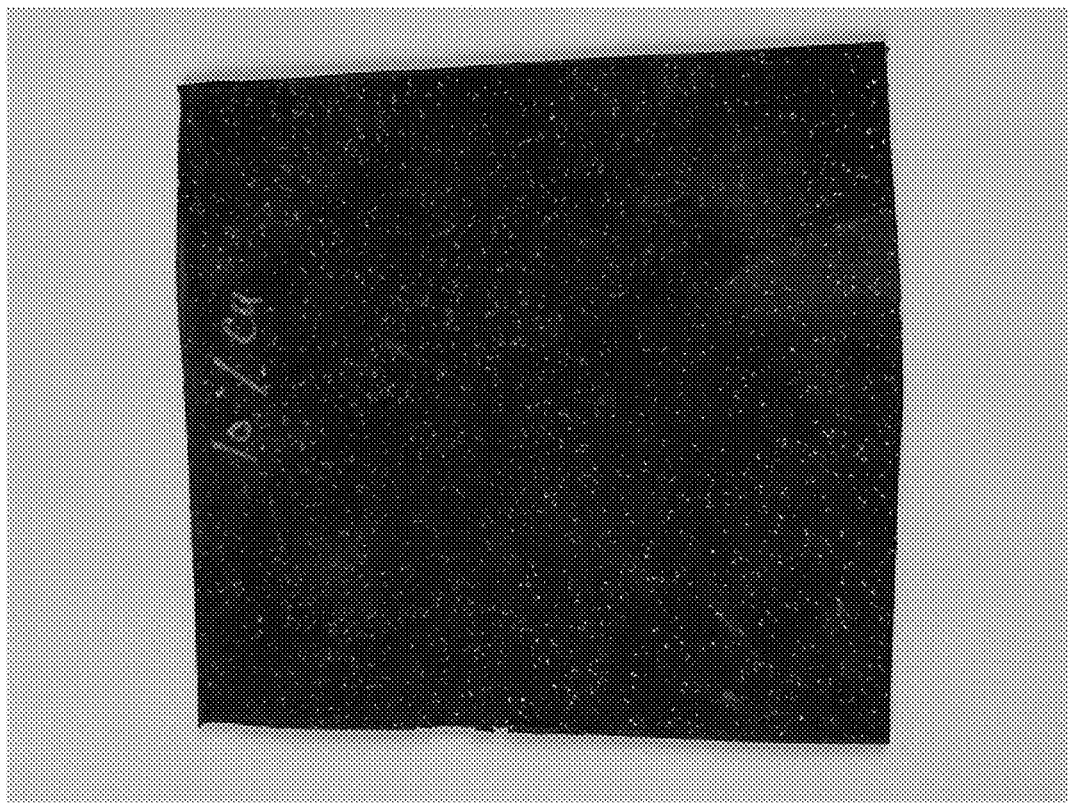
FIG. 3 is a representative image of one type of sole material containing a rubber blend and 10% copper, where the copper is dispersed as particles within the sole material.

In some cases, this document provides outsoles that include one or more metals (e.g., heavy metals, metal salts, metal compounds, metal chelates, or metal alloys) incorporated within the basic composition of the outsole. For example, an outsole can be constructed from any appropriate polymeric material that has been combined with particles of one or more metals (e.g., copper). Examples of suitable polymers include, without limitation, polyurethane (PU), silicone, polyvinyl chloride (PVC), ethyl vinyl acetate (EVA), nylon polyethylene (PE), and rubber, such as natural rubber or a vulcanized rubber. A metal-loaded polymer can include any appropriate percentage of metal. For example, a metal-polymer combination can include from about 0.1% to about 25% metal (e.g., about 0.1% to about 0.5%, about 0.5% to about 1%, about 1% to about 2.5%, about 2.5% to about 5%, about 5% to about 10%, about 10% to about 15%, about 15% to about 20%, or about 20% to about 25%). A representative image of material containing a rubber blend and 10% copper particles is shown in FIG. 3. It is noted that given the ability of metals (e.g., heavy metals such as copper) to kill bacteria and viruses even without being in direct physical contact (see, the Example below), also referred to as the "anti-infective range," it is noted that 100% of the outsole surface need not be covered with the metal in order to be effective. Thus, the percentage of metal included in a metal-loaded polymer outsole can be selected such that the metal particles are dispersed throughout the outsole, and are present at a density to provide anti-infective properties to most or substantially all of the outsole surface (e.g., at least 50%, at least 60%, at least 70%, at least 80%, at least 90%, at least 95%, or at least 98% of the surface of the outsole), depending on the size of the particles and their associated anti-infective range. Moreover, it is noted that soles constructed of metal-loaded polymers typically will have the anti-infective dispersed throughout high risk, moderate risk, and low risk areas of the sole. As portions of the sole are eroded away (e.g., by friction) during wear, metal particles that were originally located within the sole, away from the outer (e.g., ground-facing) surface, will become exposed at the outer surface and can exert their anti-infective properties. In addition, when copper is used, friction at the surface during wear can remove oxidation from previously anodized particles.

The metal particles embedded in a metal-loaded polymer matrix can have any appropriate size and shape. Various suitable shapes of the metal particles may be used (e.g., geometric shapes such as rectangular, triangular, polygonal, spherical, or the like). In some cases, the metal particles can be asymmetrically or irregularly shaped, such that they are more readily trapped and retained in the polymer portion of the sole. In some embodiments, the metal particles can have a rough or irregular surface to promote particle retention within the polymer portion. The metal particles can have an average maximum dimension of about 1 µm to about 7 mm (e.g., about 1 µm to about 5 µm, about 5 µm to about 10 µm, about 10 µm to about 20 µm, about 20 µm to about 30 µm, about 30 µm to about 40 µm, about 40 µm to about 50 µm, about 50 µm to about 100 µm, about 100 µm to about 250 µm, about 250 µm to about 500 µm, about 500 µm to about 1 mm, about 1 mm to about 3 mm, about 3 mm to about 5 mm, or about 5 mm to about 7 mm). It is noted that copper powder that can be used in the soles provided herein is available commercially from various sources (e.g., Sagwell USA Inc., Palos Verdes Estates, Calif.; and Jantz Supply Inc., Davis, Okla.). Any appropriate method of footwear manufacturing can be used make a sole containing a metal-loaded polymer, including, for example, conventional methods. In some cases, for example, metal particles can be combined with a polymer and formed into a sole using any appropriate sole molding process, such as injection molding, cold-molding, press-crosslinking processing, press molding, heat molding, and the like. It is noted that in addition to a metal and a polymeric material, a shoe sole as provided herein can include any other appropriate components (e.g., reinforcements, crosslinking agents, anti-degradants, process aids, and/or colorants).

Figure 4:
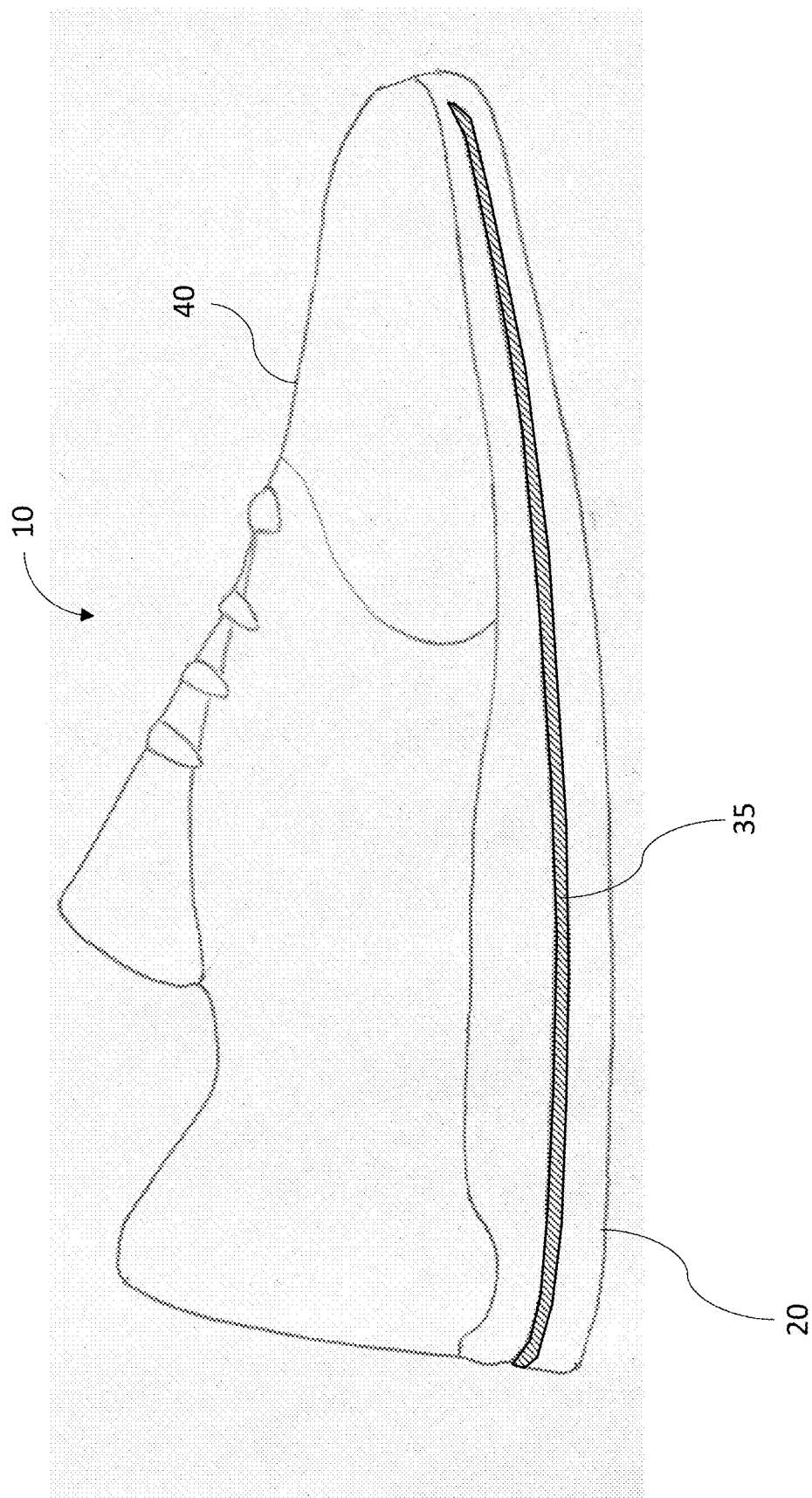
FIG. 4 is an illustration showing an embodiment of a shoe sole as provided herein.

In some cases, a sole as provided herein can include a sheet of metal that covers substantially all of the area of the sole, along with an impact weight absorbent cover positioned to contact the ground and protect the metal sheet during ambulation. An example of such a sole is depicted in FIG. 4, which includes metal inlay 35 extending laterally and transversely throughout the sole (e.g., midsole) of the shoe. In some cases, an outsole 20 or midsole 30 can include a metal (e.g., a heavy metal, heavy metal alloy, or heavy metal salt) inlay within the structure of a sole. The metal inlay can, in some cases, be visible from the external sides of the sole, as indicated by FIG. 4. The impact weight absorbent cover is the portion of the sole that touches the ground, and can include any appropriate material (e.g., natural rubber, polyurethane, or an expanded polymer foam (e.g., ethylene-vinyl acetate (EVA) foam).

Figure 5B:
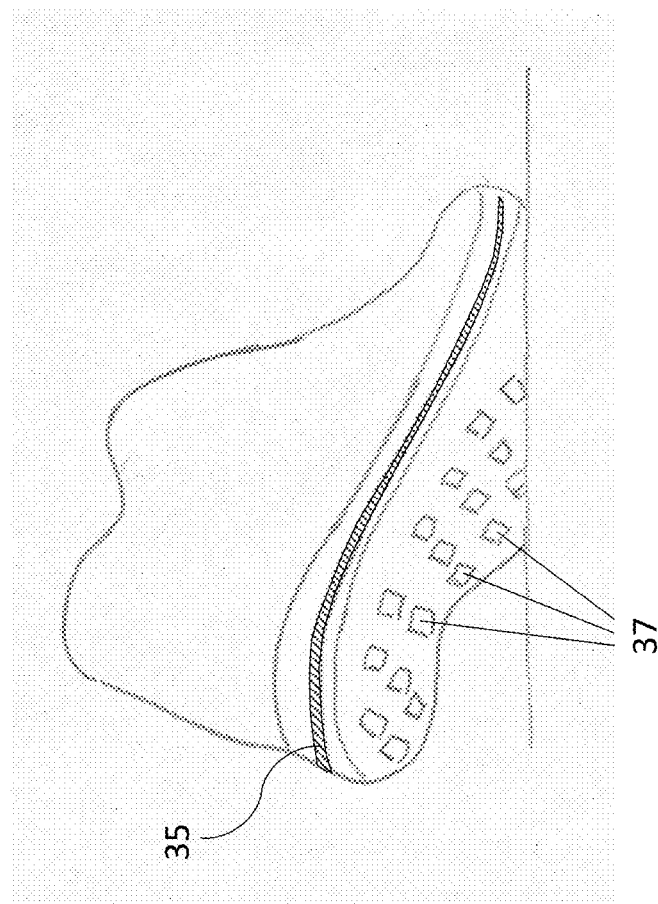
FIGS. 5A and 5B are a bottom view (FIG. 5A) and a perspective side view (FIG. 5B) of an embodiment of a shoe sole as provided herein.
Figure 5A:
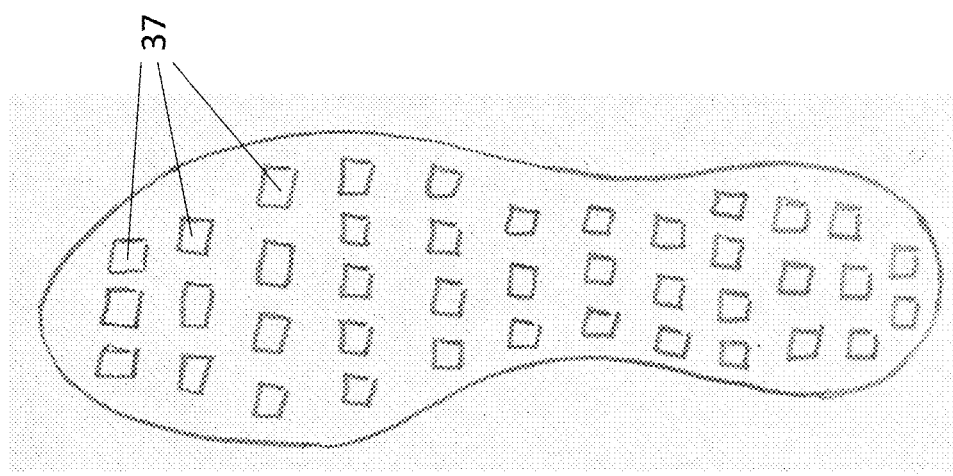
Figure 6A:
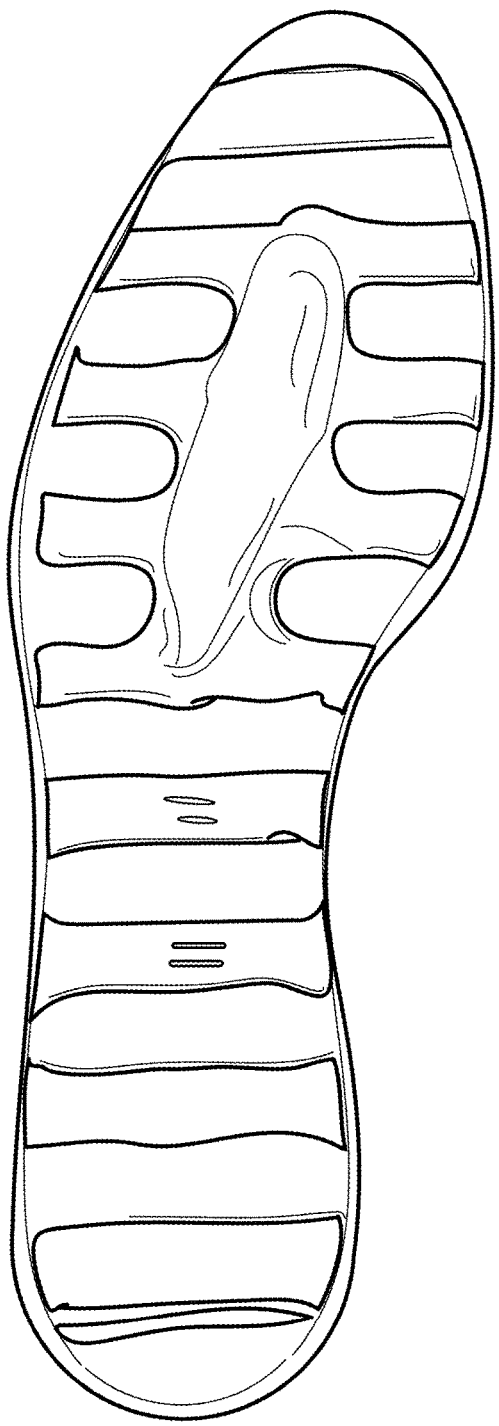
FIGS. 6A and 6B are images showing a bottom view (FIG. 6A) and a perspective bottom view (FIG. 6B) of an embodiment of a sole having attached pieces of copper sheeting.
Figure 6B:
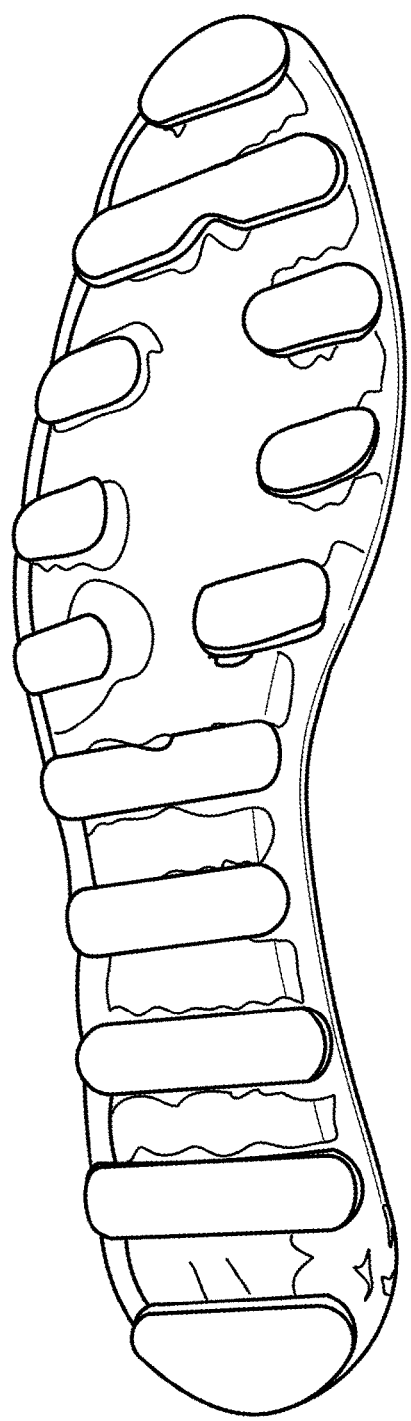
Figure 7:
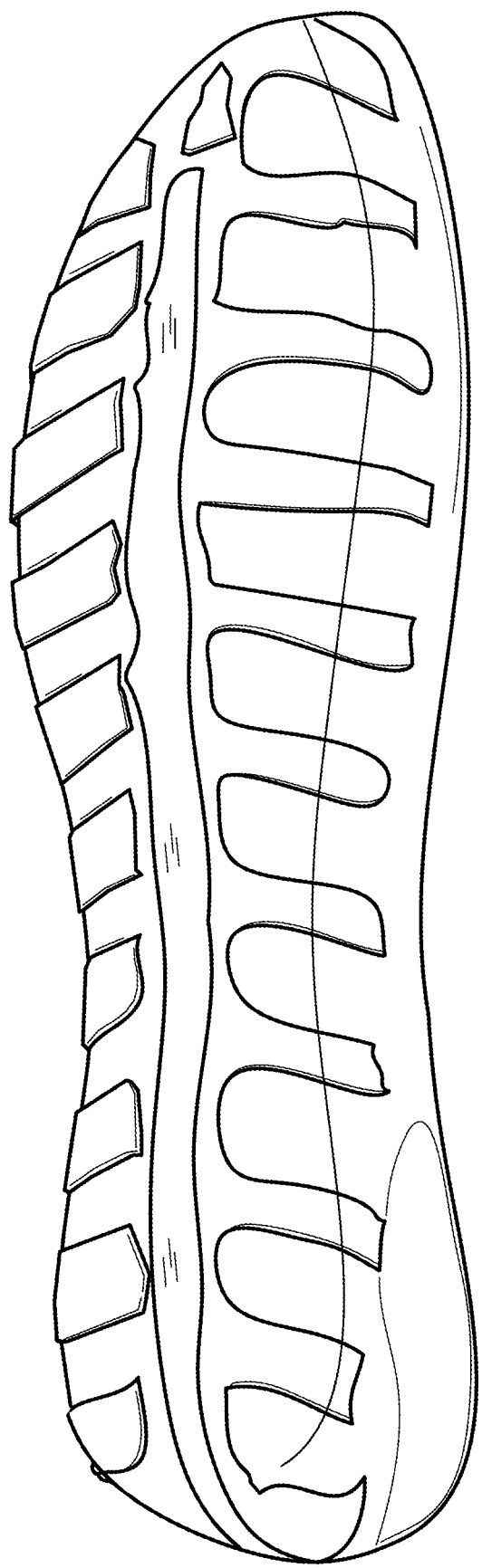
FIG. 7 is an image showing another embodiment of a sole having attached pieces of copper sheeting.
Figure 8:
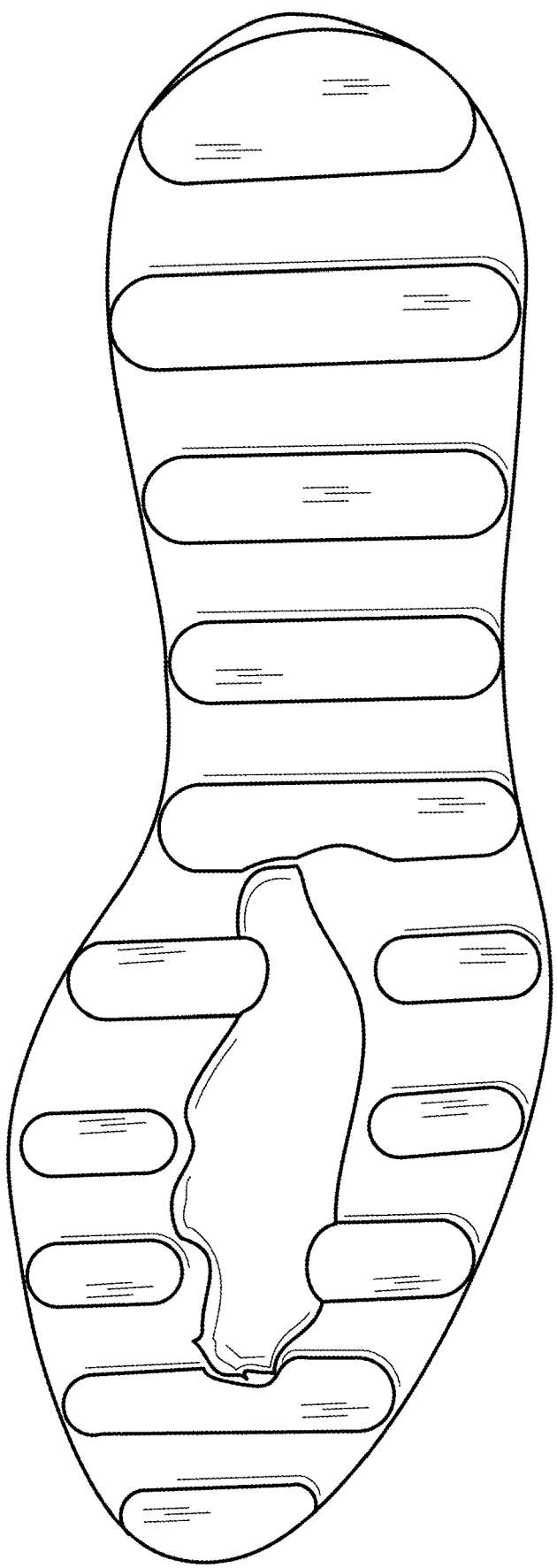
FIG. 8 is an image showing another embodiment of a sole having an attached piece of copper sheeting.
Figure 9:
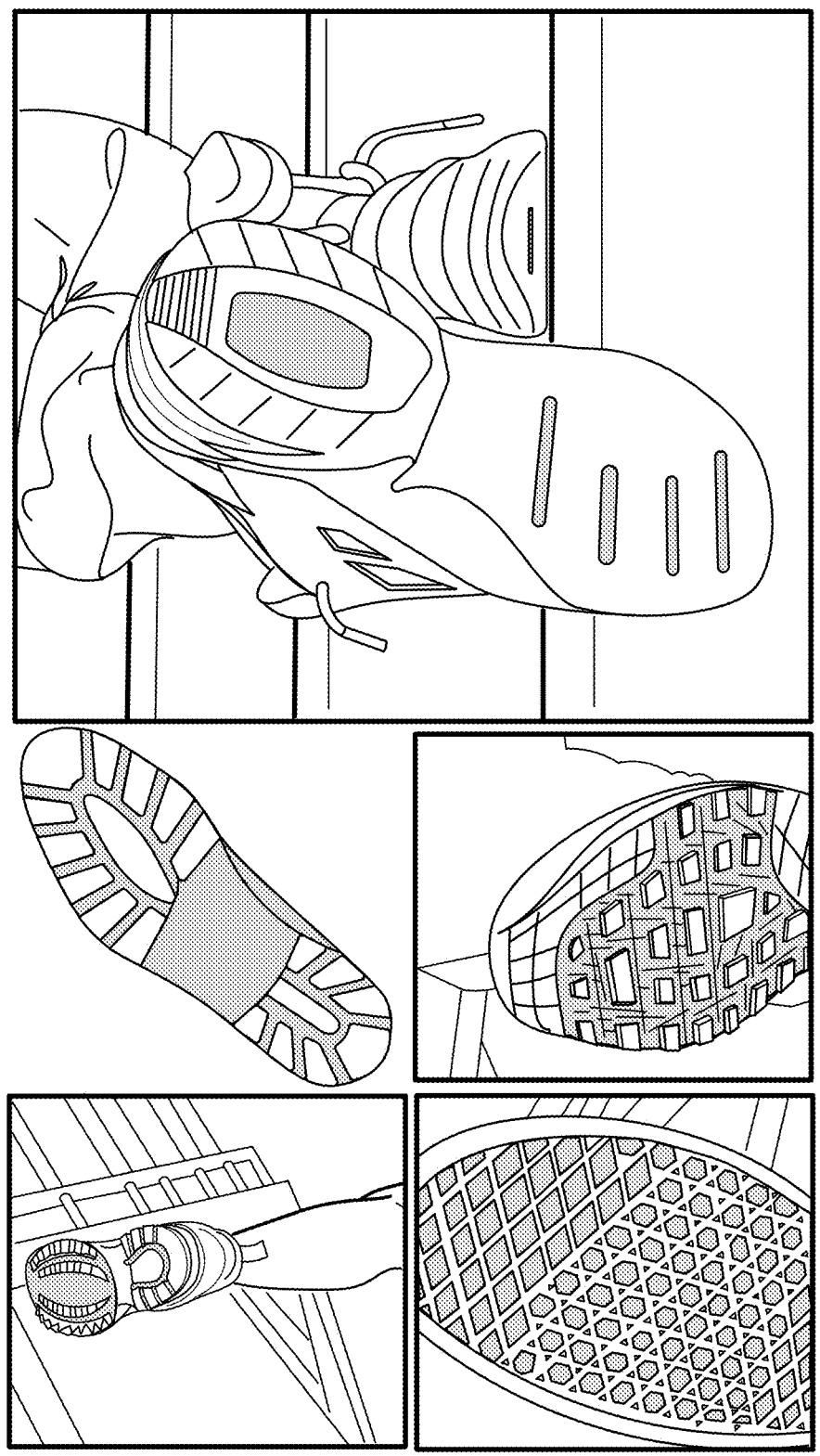
FIG. 9 is a series of images showing other embodiments of soles having attached pieces of copper sheeting.

In some cases, a sole can include one or more discrete pieces of metal (e.g., metal sheeting) fixedly coupled to a midsole and/or an outsole, such that the metal is "visible" from a surface of the shoe and can come in contact with contaminants present in the environment (e.g., on flooring or the ground). In some cases, an outsole may have openings through which a metal inlay (or a metal-containing portion) can be accessible. An example of such a sole is depicted in FIGS. 5A and 5B, which show the bottom surface of an outsole having openings through which one or more metal pieces 37 can be exposed to contaminants on the ground. In some cases, the outsole may be constructed from a flexible material that can provide comfort to the wearer, protect the metal pieces 37 from eroding or damage during use, and to protect the surface of the floor from scuffing by the metal pieces.

Figure 10:
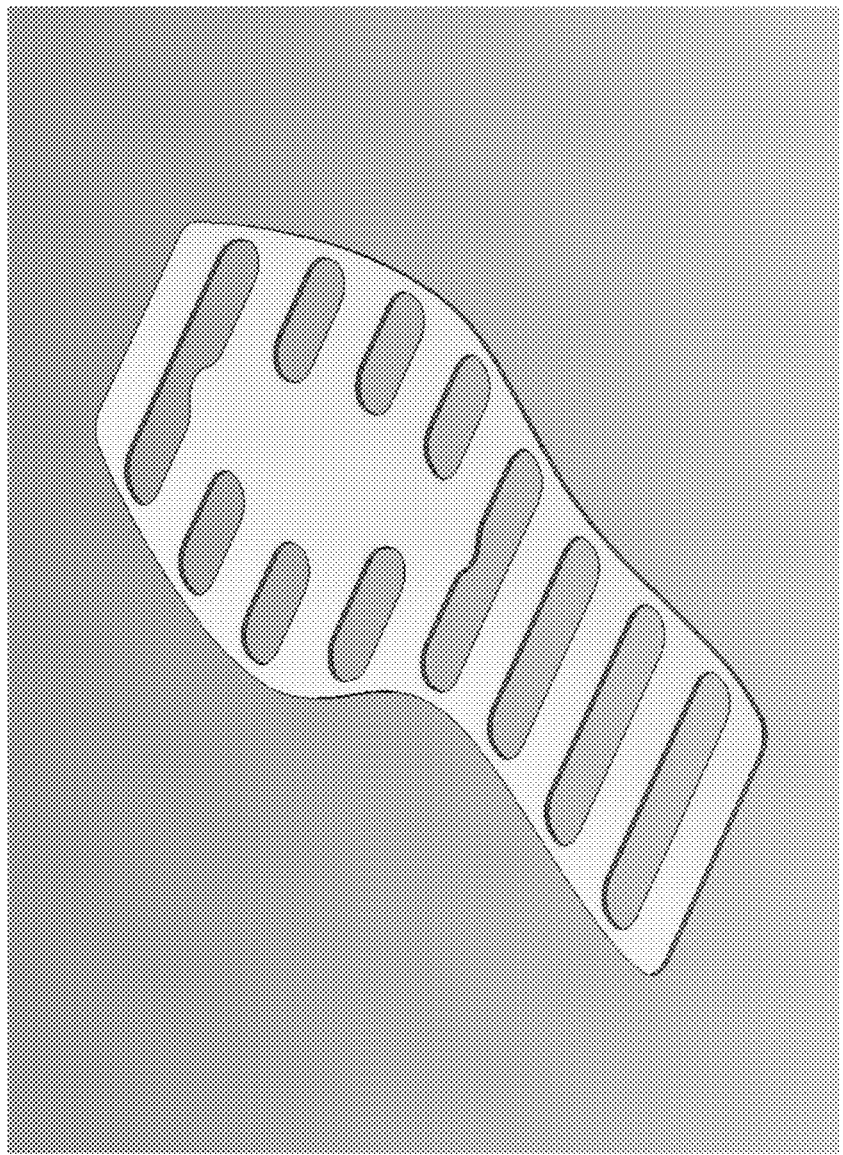
FIG. 10 is an image showing an embodiment of a metal inlay for a sole as provided herein.

In some cases, one or more discrete pieces of metal can be embedded in or attached to particular locations on the bottom of an outsole, such that the metal pieces face the ground during wear but do not directly contact the ground. For example, one or more metal pieces can be embedded in or attached to the surface of an outsole within one or more recessed areas defined by treads on the outsole. The use of discrete metal pieces, rather than a single metal piece spanning the width and length of the midsole, can permit the sole to be flexible (e.g., during ambulation). Representative examples of outsoles having copper pieces embedded therein or affixed thereto, between tread protrusions, are shown in FIGS. 6A, 6B, 7, 8, and 9. The example depicted in FIGS. 6A and 6B includes multiple pieces of copper sheeting spaced throughout the length of the sole, essentially from the toe to the heel, while the example depicted in FIG. 7 includes a single piece of copper sheeting with numerous cutouts to go around the raised treads. The example in FIG. 8 includes one relatively large piece of copper sheeting attached to the forward portion of the sole (under the portion that would support the ball of a foot), and the examples shown in FIG. 9 include other configurations with various sizes and placements of copper sheeting. An example of a metal (e.g., copper) inlay for a sole is shown in FIG. 10.

Any appropriate method can be used to attach one or more metal pieces to a shoe sole. In some cases, for example, an adhesive can be used to attach pieces of a metal (e.g., copper) to selected areas of an outsole made from any suitable material (e.g., a polymer such as PU, silicone, PVC, EVA, PE, or rubber). Adhesives that may be useful include, without limitation, rubber cement, silicone glue, and heat activated primers. In some cases, after the adhesive and metal are placed on the outsole, pressure can be applied to promote bonding. In some cases, the anti-infective metals are bonded to a shoe sole by heating bonding methods, such as injection molding, or heat-press molding. In some cases, one or more pieces of metal can be placed on an outsole (or material from which the outsole will be made), and the outsole material can be vulcanized around the metal to effectively embed the metal within the outsole. Such an attachment method can be useful in some cases, since the heat used to flow the rubber material can facilitate adhering to the metal.

Figure 11:
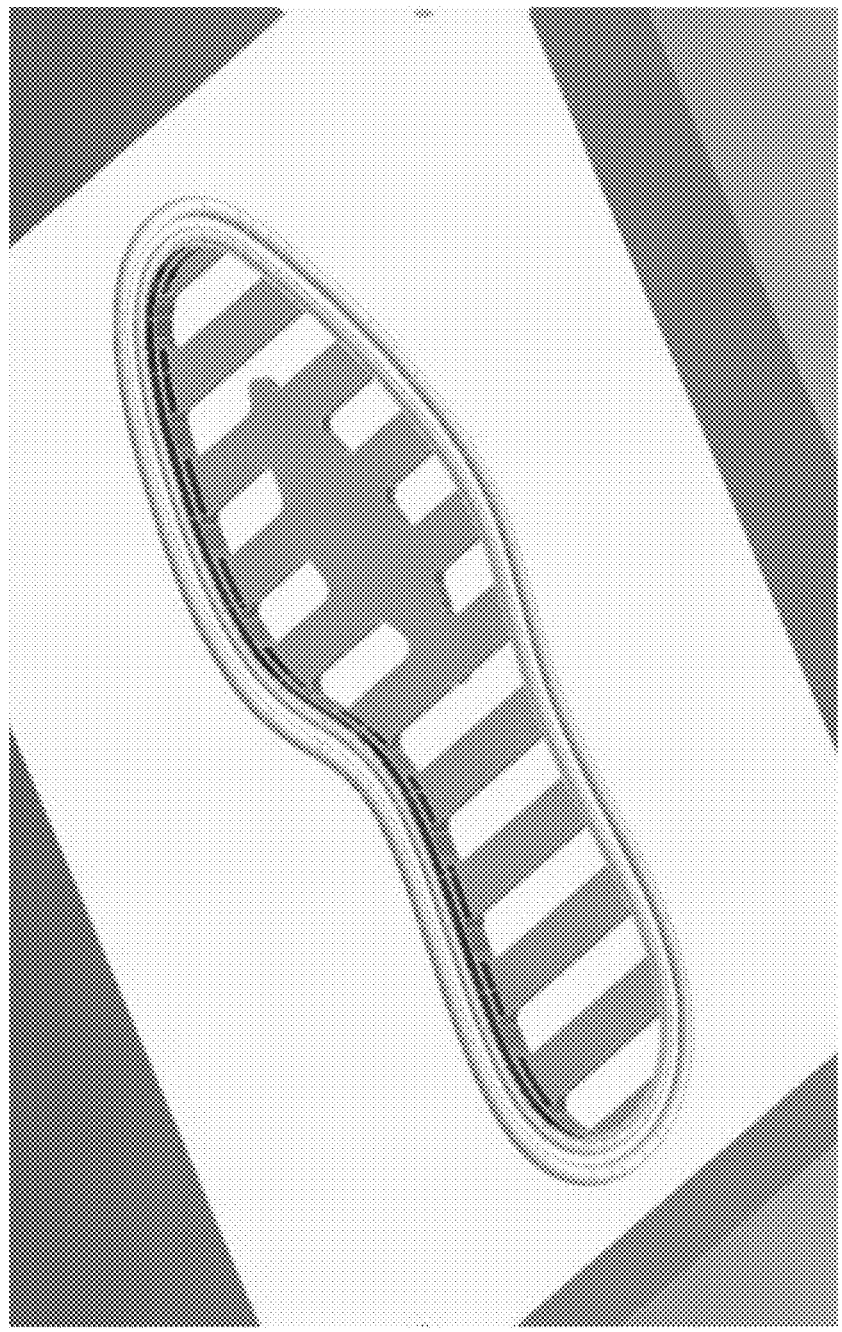
FIG. 11 is an image showing an embodiment of a mold that can be used to manufacture a sole having a metal inlay.
Figure 12:
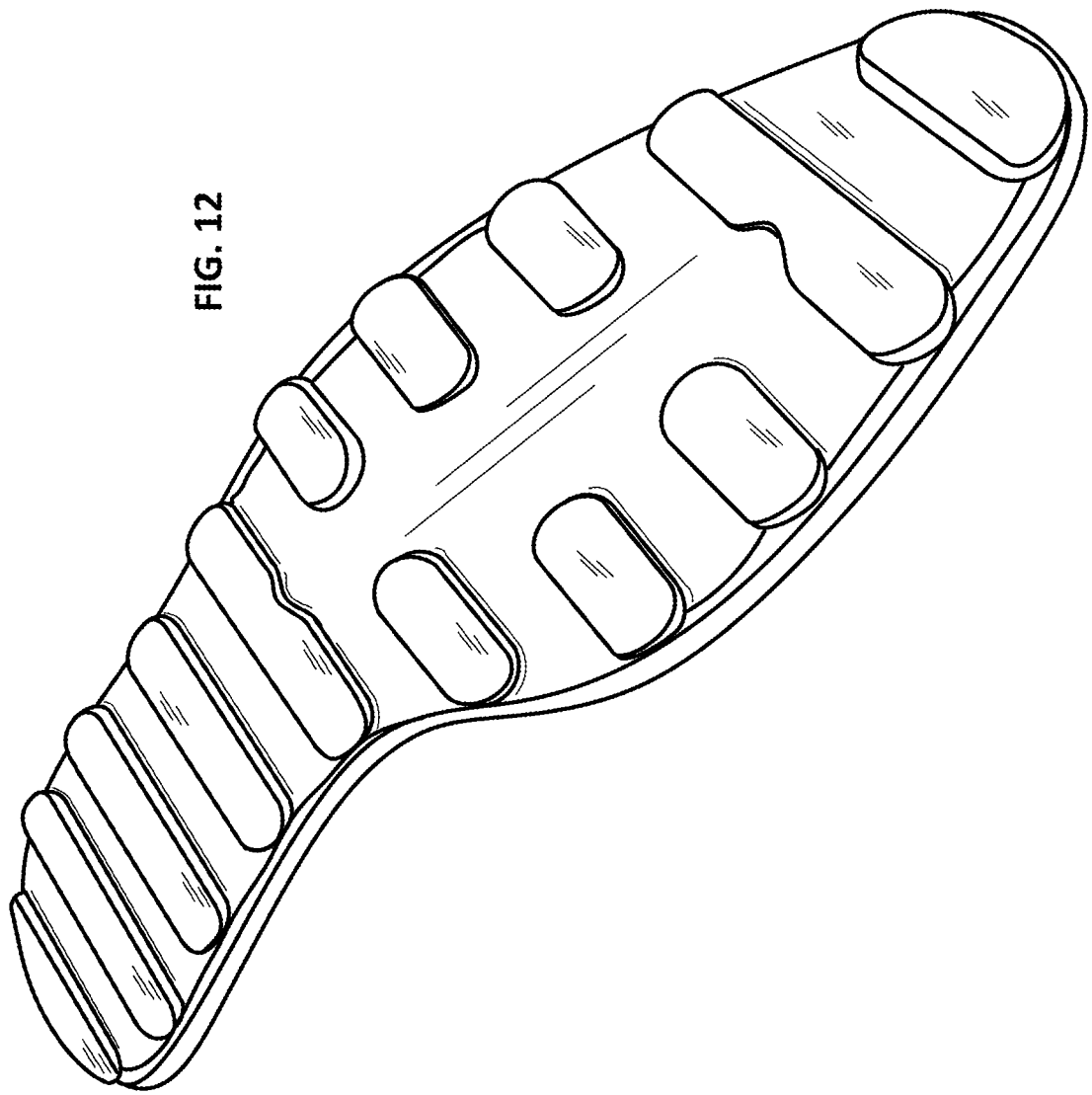
FIG. 12 is an image showing an embodiment of a sole having an integrated copper inlay, made using the inlay shown in FIG. 10 and the mold shown in FIG. 11.

In some cases, a sole containing a copper inlay can be manufactured according to the following general method. A polymeric material (e.g., a rubber compound) can be formed into an uncured preform of a particular weight and shape, depending on the design of the sole. One or more copper inserts can be die cut from a copper sheet to a desired shape and size. The copper insert(s) can be cleaned or otherwise prepared for attachment to the polymeric material. For example, the insert(s) can be sandblasted on one or both sides (e.g., using aluminum silicate sand). Alternatively or in addition, an adhesive can be placed on one or both sides of the insert(s). A compression molding process then can be used to integrate the copper insert(s) with the polymeric material. For example, the insert(s) and the polymeric preform can be placed into a mold (e.g., as depicted in FIG. 11), and the mold can be closed in order to compressed the polymeric material around the insert, causing the polymer to flow around and bond to the insert. The polymeric material and the insert can be held in the mold under high pressure and elevated temperature in order to cure the polymer, after which the sole can be removed from the mold. FIG. 12 shows a sole that might result from the use of an insert as depicted in FIG. 10 and a mold as depicted in FIG. 11.

The metal pieces used in these embodiments can have any appropriate physical characteristics. In some cases, for example, pieces of copper sheeting having a thickness of about 3 Mil to about 22 Mil (e.g., about 3 Mil to about 5 Mil, about 5 Mil to about 8 Mil, about 8 Mil to about 12 Mil, about 12 Mil to about 15 Mil, about 15 Mil to about 18 Mil, about 18 Mil to about 20 Mil, or about 20 Mil to about 22 Mil) can be used. The metal pieces can have any appropriate sizes and shapes, depending on the topography of the outsole treads, for example. Suitable metal sheeting is commercially available. For example, copper alloy sheeting containing at least 99.9% copper and not more than 0.05% oxygen is available from Basic Copper (Carbondale, Ill.).

It is noted that in these embodiments, the metal may become damaged over time (e.g., when shoes are tapped against objects, when debris kicks up from the ground, or when they become wet). The likelihood of such damage is reduced, however, by the fact that the metal components are located within recessed areas between the treads, since the portions of the treads that extend distally from the shoe by the greatest amount will incur most of the frictional damage and erosion during use.

In some embodiments, the shoe soles provided herein can be made from a metal-loaded polymer, and also can include one or more pieces of embedded or attached metal. For example, an outsole can include a combination of a metal inlay and a metal-loaded sole material. Such soles may be particularly effective for killing infectives, as they can provide an even higher metal surface area and associated effective range than either the inlay or metal-loaded polymer option individually. In some cases, should a single layer erode (e.g., from frictional wear), a secondary underlayment can add a backup layer of protection to the wearer.

This document also provides shoe soles (e.g., outsoles) that include a member with a first end and a second end, where the first end is opposite the second end in a longitudinal direction, and where the member has a first surface attachable to a shoe component, an intermediate surface, and a plurality of projections extending from the intermediate surface in a transverse direction. Each projection can extend from the intermediate surface to a distal-most predetermined height, where the distal-most predetermined heights of the projections together define a distal surface of the sole. The predetermined height can be, for example, at least about 0.1 mm (e.g., at least about 0.5 mm, at least about 1 mm, at least about 2 mm, at least about 3 mm, at least about 4 mm, about 0.1 to about 5 mm, about 0.1 to about 0.5 mm, about 0.5 to about 1 mm, about 1 to about 2 mm, about 2 mm to about 3 mm, about 3 mm to about 4 mm, or about 4 mm to about 5 mm). Each projection also can have one or more surfaces at heights that are less than the distal-most predetermined height, where the surfaces at heights less than the distal-most predetermined height define proximal (non-ground contacting) surfaces of the sole. An anti-infective agent can be present on one or more of these proximal surfaces. For example, the anti-infective agent can be disposed on non-ground contacting regions in order to prevent the anti-infective agent from becoming removed from the sole of the shoe due to normal use.

This document also provides outsoles that are configured to be attached to a shoe by a consumer or a vendor. In some cases, the outsoles can include a polymer with embedded or attached pieces or particles of metal, as described above. In some cases, the outsoles can include strips or other pieces of metal (e.g., heavy metal, heavy metal salt, or heavy metal alloy), where the strips or pieces can be applied to or placed into the soles of pre-existing shoes using a means for attachment (e.g., an adhesive or one or more fasteners, such as hooks, tacks, staples, hook and loop (e.g., VELCRO®) fasteners, or the like).

In some cases, a metal material can be included in the upper part of the shoe. For example, metal threads (e.g., threads containing copper, silver, or any other appropriate metal) can be woven into the upper part of a cloth shoe, or can be used in the stitching between shoe parts.

The invention will be further described in the following examples, which do not limit the scope of the invention described in the claims.

EXAMPLES

Studies were conducted to determine whether a copper-faced outer shoe sole could create an active, antibacterial barrier that mitigates transmission of pathogens in high risk environments. In particular, experiments were carried out to test the biophysical features of "copper-cide"—particularly how far copper diffuses into a small physical space or three-dimensional area in order to exert its antimicrobial action.

Figure 13:
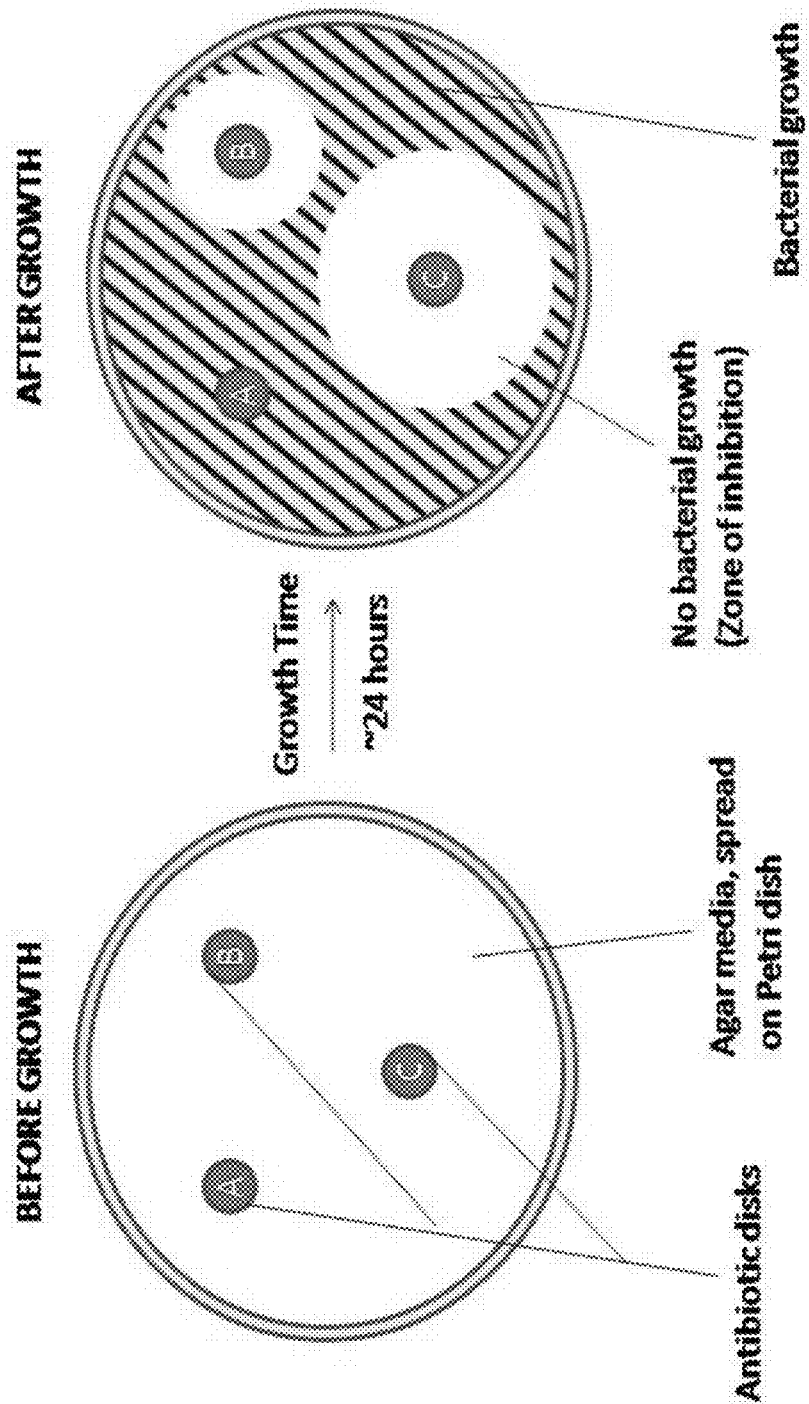
FIG. 13 is a schematic illustrating a Kirby-Bauer Disk Diffusion test. Bacterial cells are plated from a broth culture onto sterile agar petri dishes, and antibiotic soaked paper disks (or control disks without antibiotic) are placed directly on the dish. After 24 or more hours, a confluent layer of bacteria appear to grow up on the dish. Clearing or clear but hazy zones indicate antibiotic sensitivity of the test microbe. The size of the killing zone reflects how well the antibiotic diffuses into the agar and sensitivity of the organism.

In some studies, a disk-diffusion test was used as a model for testing diffusion and bacterial targeting (FIG. 13). This method is used, for example, to screen for antibiotic sensitivity in clinical microbiology laboratories. An agar plate was first spread with an axenic culture of bacteria, and then paper disks containing different antibiotics or test agents were placed on the agar surface. The bacteria were allowed to grow on the agar media, and growth was observed using a simple read-out: a zone of clearing around a disk indicated no bacterial growth, and conversely, the lack of a clearing perimeter indicated bacterial resistance. Control disks without antibiotic or effector were included to demonstrate that the test was reporting accurately. The results of such tests generally are clear cut and sensitive. In some cases, a bacterial kill zone can be "hazy" but still discernable as a clearing if the test drug on the paper disk displays weak bacterial killing.

Figure 14B:
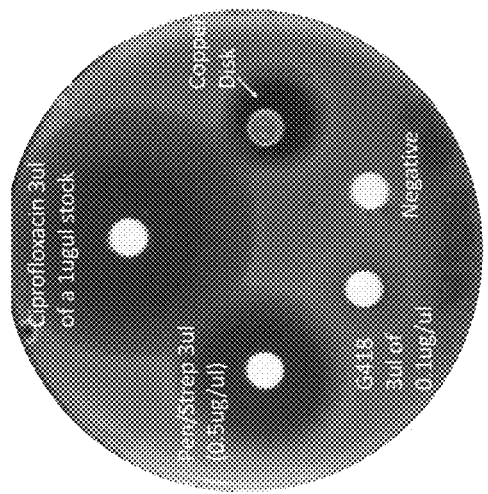
FIG. 14B is an image showing the results of a Disk Diffusion test with *Escherichia coli* cultured in the presence of copper, penicillin/streptomycin, ciprofloxacin, or G418. Again, inhibitory zones appear darker and clear.
Figure 14A:
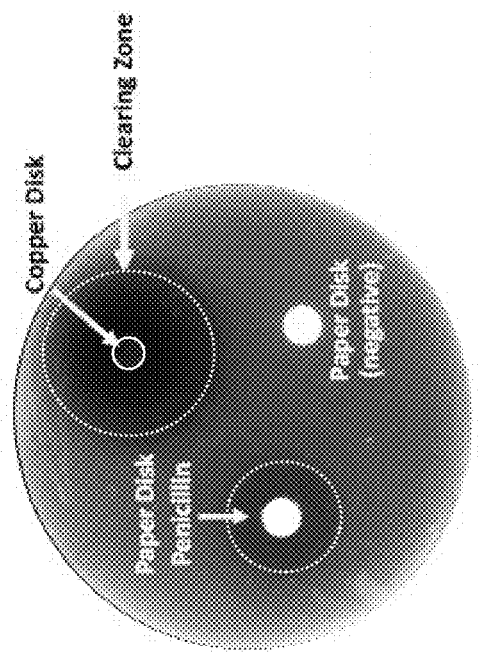
FIG. 14A is an image showing the results of a Disk Diffusion test with *Pseudomonas aeruginosa* (PAO). Three disks were placed on a PAO/agar overlay culture: a penicillin-soaked paper disk, a negative control (no treatment) paper disk, and a sterile punch disk of pure elemental sheet copper, and the culture was incubated for 24 hours. Zones of inhibition are marked as clearing zones (dashed circles) where bacterial growth was stunted. The bacterial growth area appears hazy (see the negative control disk), while inhibitory zones appear darker and clear.

In one test, *Pseudomonas aeruginosa* (PAO) was used to examine copper sensitivity. PAO is an opportunistic organism that typically is found on human skin. PAO can adversely affect higher risk individuals such people who are immuno-compromised, organ transplant patients, cancer patients, the elderly, or infants. In the first experiment, PAO was grown overnight in a broth culture. The next day, the culture was mixed with 1% agar at 37° C., and a uniform layer of the mixture was poured onto an LB agar petri dish, and allowed to solidify. The time of plating was designated as time zero ($T_0$). Three disks were placed on top of the agar overlay: a penicillin-soaked 3M paper disk, a negative control (no treatment) disk, and a 6 mm sterile punch disk of pure elemental sheet copper (0.8 mm thick). All disks were marked on the plate. The culture was incubated for 24 hours in a 37° C. incubator and then removed from the incubator and photographed (FIG. 14A). The negative control disk showed no zones of clearing. The penicillin disk showed a clearing that extended 5-7 mm from the edge of the 6 mm disk. This indicated that PAO was quite sensitive to the antibiotic and that sensitivity extended to 6 mm, due to diffusion of the antibiotic. Penicillin is a rather large molecule with a mass over 330 g/mol. In general, larger molecules tend to be diffusion-limited. In contrast, copper is an inorganic atom with an atomic mass of 63 g/mol. Given its small mass and ionic charge ($Cu^{++}$ in aqueous form) it will diffuse through the agar to a much greater extent. As shown in FIG. 14A, the copper killing zone of PAO was significantly larger (25 mm) than the 6 mm killing zone for the higher molecular mass penicillin. This suggested that PAO is particularly sensitive to oxidative DNA damage by copper, even more so than penicillin. A plate from a similar study using *E. coli* strain Rosetta incubated for 18 hours in the presence of copper, penicillin/streptomycin, ciprofloxacin, and G418 showed that the copper disk also was similarly toxic toward a laboratory strain (FIG. 14B).

Figures 15A, 15B:
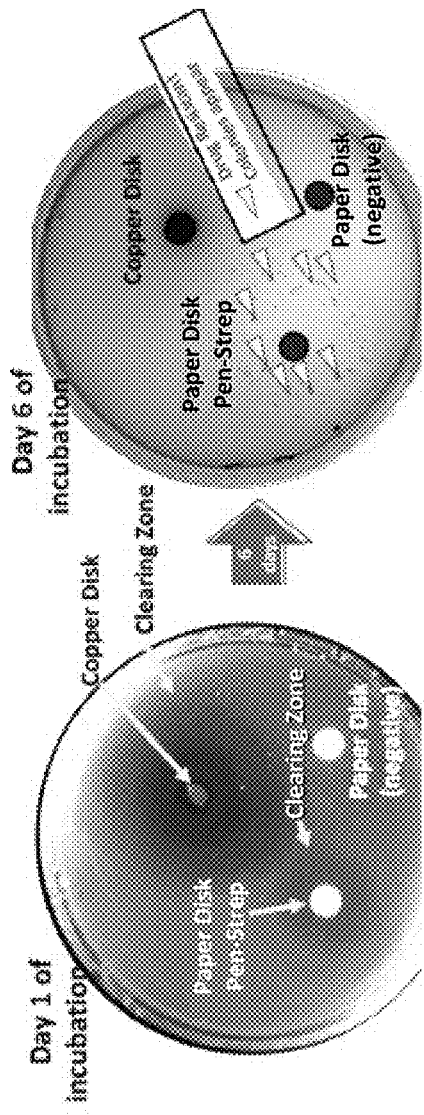
FIGS. 15A and 15B are images showing the results of a Disk Diffusion test with MRSA (methicillin resistant *Staphylococcus aureus*) after one day (FIG. 15A) and six days (FIG. 15B) of incubation. Drug-resistant colonies appeared around the penicillin-streptomycin disk after 6 days of selection, but there were no resistant colonies around the copper disk.

The pathogen MRSA (methicillin resistant *S. aureus*) also was tested. MRSA infections are caused by a type of staph bacteria that has become resistant to many of the antibiotics used to treat ordinary staph infections. Most MRSA infections occur in clinical care environments. For this experiment, MRSA was plated to test the combination of penicillin and streptomycin, in addition to testing copper. In theory, the MRSA should have responded more strongly to the streptomycin than the copper. The cultures were incubated up to 6 days (FIG. 15B), as the extended incubation would be a sufficient time for the appearance of streptomycin resistant strains. These appeared as isolated colonies near the antibiotic-loaded disk. FIG. 15A shows clearing zones about 5 mm wide around the pen-strep disk, and clearing zones greater than 20 mm wide around the copper disk after one day of incubation. Like the PAO results, the MRSA was highly sensitive to copper exposure. FIG. 15B shows antibiotic resistance, with clones appearing around the pen-strep disk but none appearing around the copper disk during the six-day study. This was a clear demonstration of how the bacteria developed resistance to antibiotics, but did not develop resistance to copper.

Figure 16:
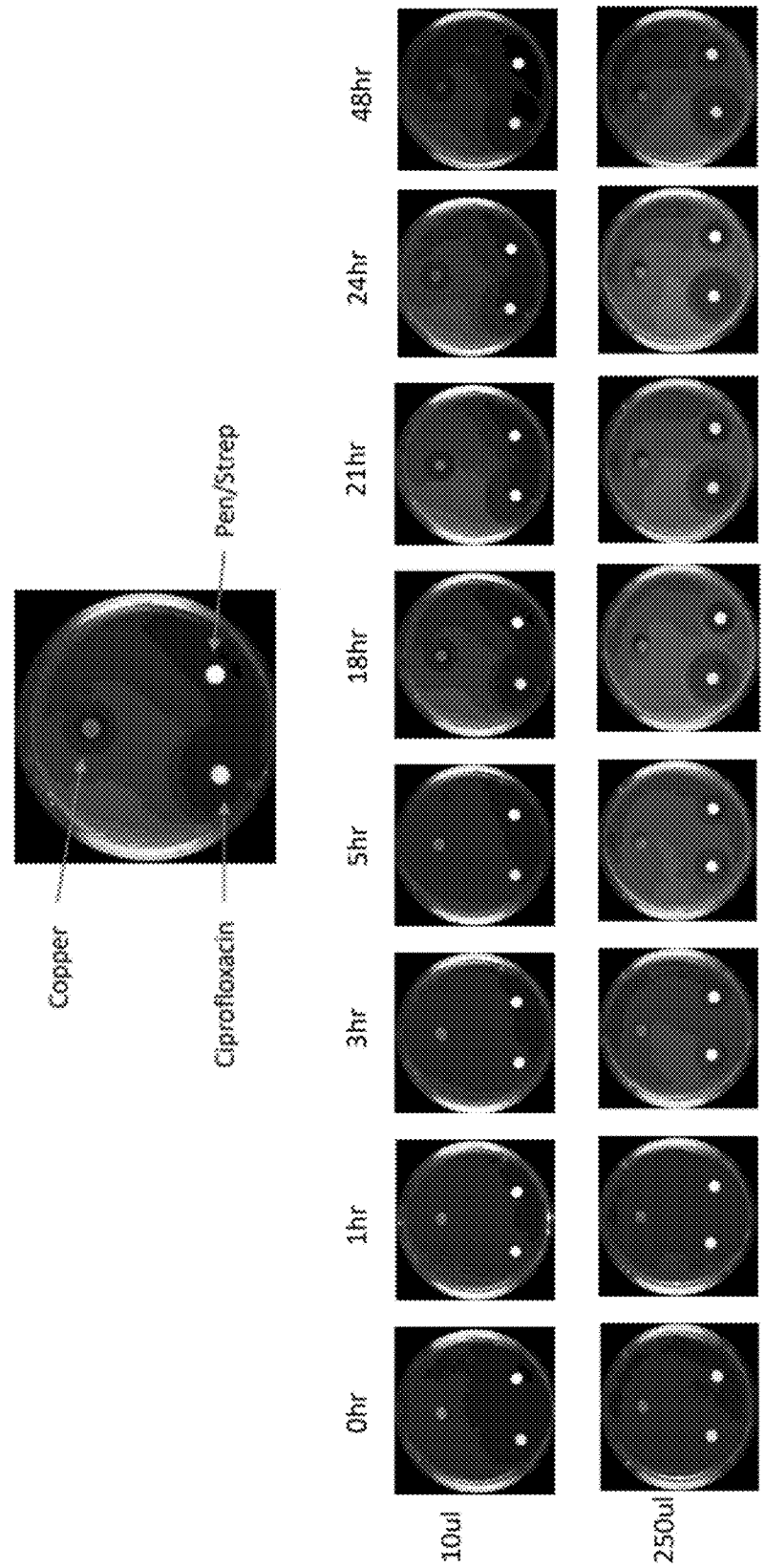
FIG. 16 includes images of plates from Disk Diffusion tests with *E. coli* cultured up to 48 hours in the presence of copper, ciprofloxacin, and penicillin/streptomycin.

In studies with *E. coli* strain Rosetta, cells were grown overnight in growth media (TSB), and 10 µl or 250 µl of the culture were spread onto TSB agar plates using the top agar overlay method. Paper disks soaked with penicillin, streptomycin, or ciprofloxacin were then placed on the plates, as was a copper disk. The plates were incubated at 37° C. for 24 hours, and photographs were taken at 0, 1, 3, 5, 18, 21, 24, and 48 hours (FIG. 16). After 48 hours, the plates were left at room temperature, and were monitored until the 72 hour point. Strikingly, the kinetics of clearing around each disk were very similar for the comparator antibiotics and copper, again suggesting strongly that copper is mechanistically bactericidal rather than bacteriostatic (growth inhibiting).

Figure 17:
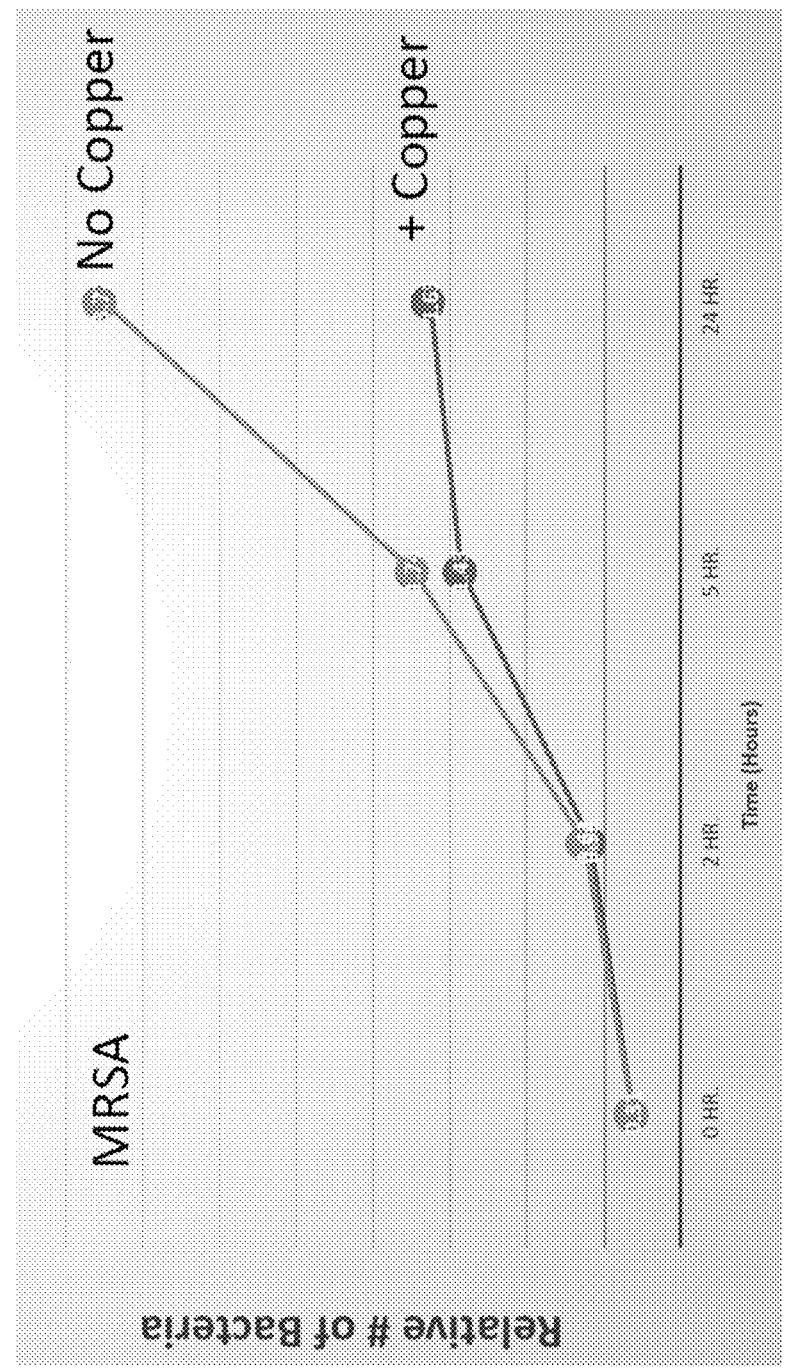
FIG. 17 is a graph plotting the growth of MRSA in liquid cultures of LB growth medium, in the presence of copper or negative control.

Further studies were conducted using liquid cultures. A copper disk was placed in a test tube in a small volume of LB growth medium. A paper disk was added to LB medium in another tube, as a negative control. Both tubes were inoculated with MRSA, and bacterial grown was followed for 24 hours to test the effect of copper on the early stages of the growth curve. As shown in FIG. 17, copper inhibited early proliferation and extended the lag phase of cell growth curve. This was an important observation, because it showed that copper could inhibit bacterial proliferation as soon as the bacteria are present as cross contaminants (e.g., on the bottom of a shoe or outer sole). Thus, in the presence of copper, potential pathogens are likely to have trouble establishing a high yield infectious outcome.

Figure 18A:
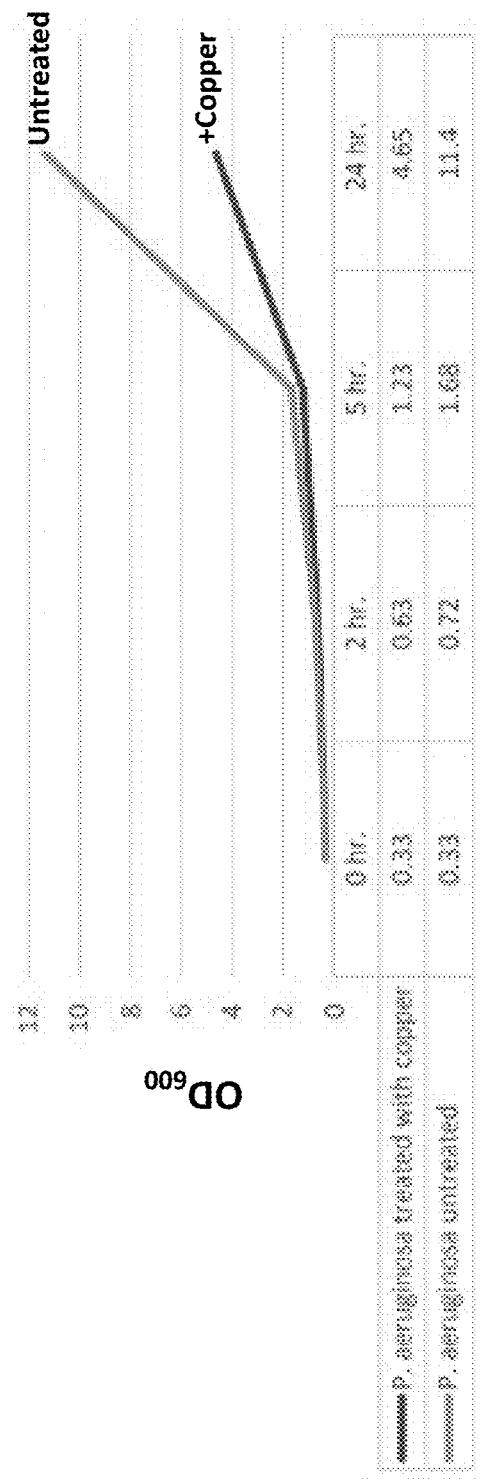
FIGS. 18A-18C are graphs plotting growth of *P. aeruginosa* (FIG. 18A), *E. coli* (FIG. 18B), and *S. aureus* (FIG. 18C) in liquid tryptic soy broth (TSB) culture, in the presence or absence of a copper disk.
Figure 18B:
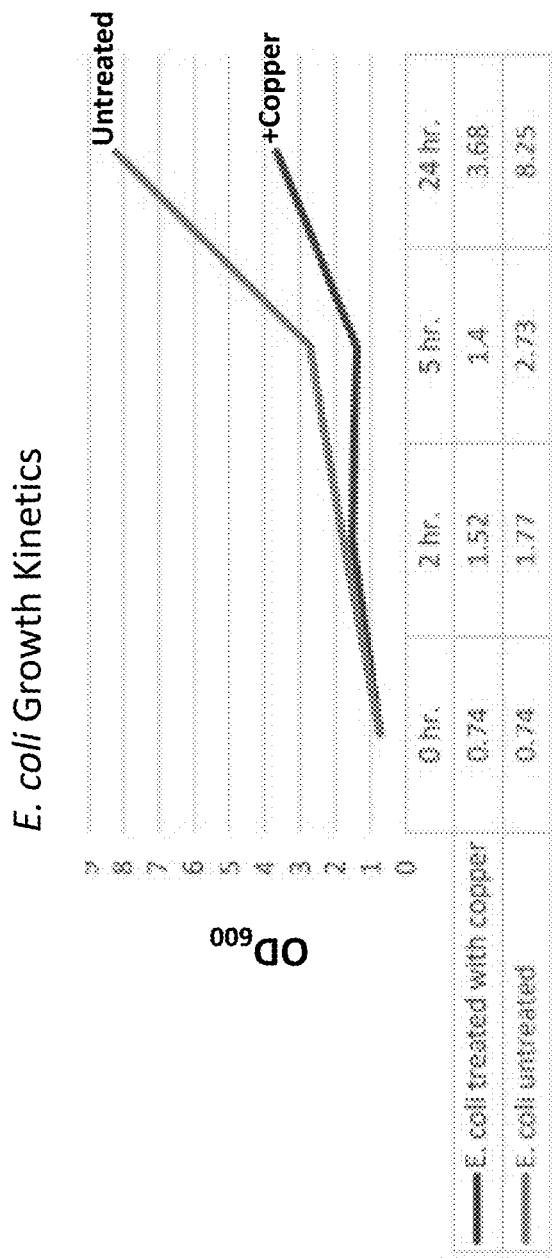
Figure 18C:
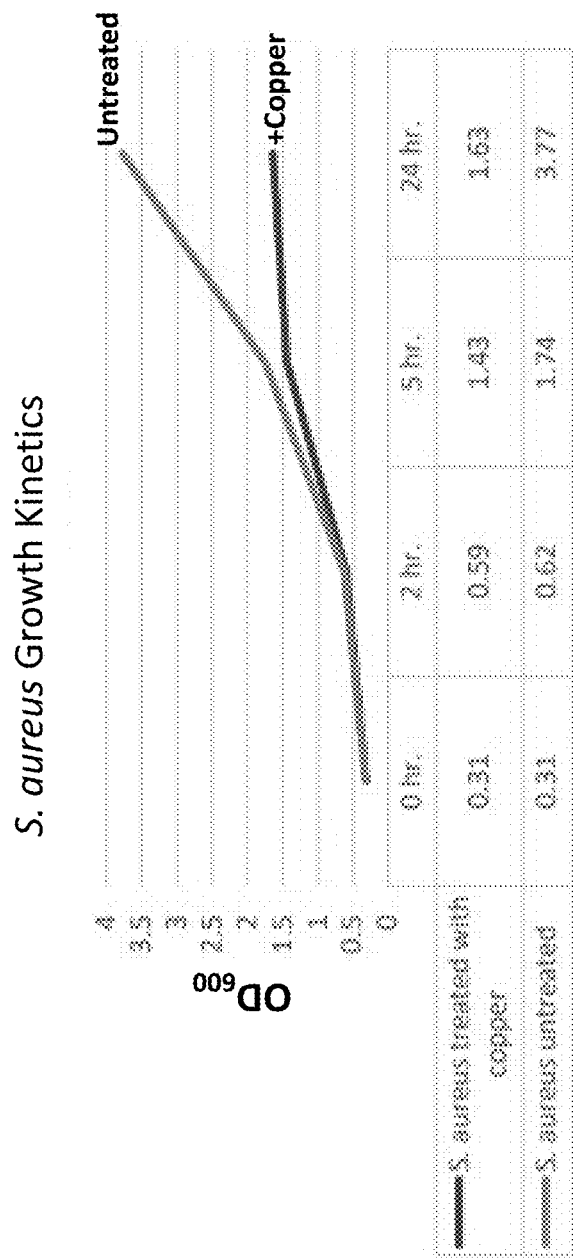

In additional studies, *P. aeruginosa, E. coli*, and *S. aureus* strains were grown overnight in TSB, and 250 µl of each culture were placed into 2 mL of TSB in a polypropylene round-bottom test tubes containing either a negative control paper disk or a copper disk. The cells were cultured at 37° C. with shaking at 300 rpm for 24 hours, and $OD_{600}$ was measured using a NanoDrop spectrophotometer at 0, 2, 5, and 24 hours. The results are plotted in FIGS. 18A-18C. In each case, cells treated copper had a significantly lower growth rate than cells that were left untreated.

Still further studies utilized copper "boats" to test the effectiveness placing bacteria directly on copper. The copper boats were autoclaved and placed in Petri dishes containing molten agar to seal the boats into place. A third "boat" of PARAFILM® was used as a negative control. *E. coli* strain Rosetta was grown up in a broth culture for 18 hours, and 50 µl of the culture ($OD_{600}$ 4.31) was placed with in each of the three boats. All three plates were incubated at 37° C. for 24 hours, but one copper boat was allowed to "dry out" by a short incubation, while the other copper boat (and the PARAFILM® boat) remained in liquid culture. After 24 hours, 50 µl of sterile TSB was added to the dry copper plate and cells were resuspended. Samples were collected from each plate and serial dilutions were performed to quantify bacterial titers (viable bacterial cells/mL). Specifically, 10 µl of suspension were added to 1 mL of TSB to make a 1:100 dilution, and then 10 µl of that dilution was added to 1 mL of TSB to achieve 1:1000 dilution. This was repeated until a dilution of $1:10^5$ was attained. One (1) mL of each dilution was streaked on a fresh plate, which was then incubated at 37° C. for 24 hours. Images of each plate were taken and colonies were counted.

These studies clearly showed that elemental sheet copper was a highly effective anti-microbial agent under the experimental conditions, as the titer of bacteria dropped from >$10^8$/mL to less than 100 viable cells/mL (FIG. 19). Bacteria in solution and in dry form were equally targeted by copper exposure. The reduction in viability by more than 4 orders of magnitude attested strongly to the efficacy of copper in killing bacteria.

The studies described above demonstrate that copper is an effective and active anti-bacterial barrier, without the risk of developing resistance. Reasonable assumptions about the linear kill radius of copper can be made based on the data presented herein. Looking at the tread configuration and micro-topography of the shoes and outsoles provided herein, for example, these studies suggested that copper is effective in the recessed regions of the soles. The disk sensitivity data also showed that copper can exert its bactericidal effect over a rather wide range (from 5 to 20 mm). Copper, like many antimicrobial agents, requires a certain amount of time (generally in the range of minutes) to exert its influence. In a real-world situation, if small amounts of bodily fluid were to get entrapped in a retention area, it is likely that small volumes (5-100 µL) would dry and turn to a crusty material, depending on the protein content. This would enhance exposure to the copper substrate, which would naturally improve the bactericidal effect. It is noted that in the absence of the copper effect, the desiccated and trapped pathogen in the recessed areas of a sole would be stabilized due to the presence of protein or blood material. Thus, copper is especially important in situations where contaminants may dehydrate and upon entry to the home environment, might be rehydrated with negatively synergistic outcomes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A sole structure for an article of footwear, the sole structure comprising:
   a member defining a foot-supporting surface and a ground-facing surface, the ground-facing surface comprising:
   ground contacting regions; and
   non-ground contacting regions,
   wherein one or more of the non-ground contacting regions comprises an anti-infective agent, wherein the anti-infective agent comprises a metallic material, wherein a discrete piece of sheeting of the metallic material is fixedly coupled to the member, such that the metal sheeting is present on one or more non-ground contacting regions of the member, wherein the discrete piece of metal sheeting is an inlay between layers of the member, and wherein the sole structure defines an opening through which the metal inlay is visible from the ground facing surface.

2. The sole structure of claim 1, wherein the anti-infective agent is effective to inactivate or kill pathogenic biological agents disposed on the sole structure, and wherein the pathogenic biological agents are selected from the group consisting of bacteria, viruses, fungi, and yeast.

3. The sole structure of claim 2, wherein the anti-infective agent is effective to inactivate or kill from about 50% to about 99% of the pathogenic biological agents.

4. The sole structure of claim 2, wherein the anti-infective agent is effective to inactivate or kill the pathogenic biological agents within about 5 minutes to about 24 hours.

5. The sole structure of claim 1, wherein two or more of the non-ground contacting regions comprise a discrete area incorporating the anti-infective agent, wherein each discrete area is generally spaced apart from a nearest neighboring discrete area by no more than a predetermined distance, and wherein the predetermined distance is from 0.1 mm to 50 mm.

6. The sole structure of claim 1, wherein the ground-facing surface comprises a plurality of projections, wherein the ground contacting regions are defined by a distal most predetermined height of the projections, and wherein the non-ground contacting regions are defined by surfaces of the projections at heights that are less than the distal most predetermined height.

7. The sole structure of claim 1, wherein the metallic material comprises copper, a copper alloy, a coordinated copper complex, a copper-containing compound, or a copper chelate.

8. The sole structure of claim 1, wherein the sole is an outsole or a midsole.

9. The sole structure of claim 1, wherein the member comprises a flexible material, and wherein the flexible material comprises a polymer selected from the group consisting of natural rubber, a vulcanized rubber, polyurethane, and silicone.

10. A sole structure for an article of footwear, the sole structure comprising a member having a first end and a second end that is opposite the first end in a longitudinal direction, the member defining a foot-supporting surface and a ground-facing surface, wherein the member comprises a polymer and an anti-infective agent dispersed throughout the polymer, wherein the anti-infective agent comprises a metallic material, wherein the member further comprises a discrete piece of sheeting of the metallic material fixedly coupled thereto such that the metal sheeting is present on one or more non-ground contacting regions of the member, wherein the discrete piece of metal sheeting is an inlay between layers of the member, and wherein the sole structure defines an opening through which the metal inlay is visible from the ground facing surface.

11. The sole structure of claim 10, wherein the anti-infective agent is effective to inactivate or kill pathogenic biological agents disposed on the sole structure, and wherein the pathogenic biological agents are selected from the group consisting of bacteria, viruses, fungi, and yeast.

12. The sole structure of claim 10, wherein the metallic material comprises copper, a copper alloy, a coordinated copper complex, a copper-containing compound, or a copper chelate.

13. The sole structure of claim 10, wherein the member is an outsole or a midsole.

14. The sole structure of claim 10, wherein the polymer is selected from the group consisting of natural rubber, a vulcanized rubber, polyurethane, and silicone.

15. The sole structure of claim 10, wherein the anti-infective agent dispersed throughout the polymer comprises a plurality of irregularly-shaped particles of said metallic material.

16. An article of footwear, comprising:
an upper; and
a sole structure engaged with the upper, the sole structure including: a member having a first end portion and a second end portion that is opposite the first end in a longitudinal direction, the member defining a foot-supporting surface and a ground-facing surface, the ground-facing surface comprising:
ground contacting regions; and
non-ground contacting regions,
wherein one or more of the non-ground contacting regions comprises an anti-infective agent, wherein said anti-infective agent comprises a metallic material, wherein a discrete piece of sheeting of the metallic material is fixedly coupled to the member, such that the metal sheeting is present on one or more non-ground contacting regions of the member, wherein the discrete piece of metal sheeting is an inlay between layers of the member, and wherein the sole structure defines an opening through which the metal inlay is visible from the ground facing surface.

17. The article of footwear of claim 16, wherein the member is a coupleable member that attaches to an outsole fixedly attached to the upper.

18. The article of footwear of claim 16, wherein the member is an outsole or is fixedly attached to the outsole.

19. The article of footwear of claim 16, wherein the non-ground contacting region is located at the first end portion, the second end portion, a mid-portion located between the first end portion and the second end portion, or combinations thereof, wherein the first end portion is a toe location of the article of footwear, and wherein the second end portion is a heel location of the article of the footwear.

20. The article of footwear of claim 16, wherein the member comprises a polymer, and wherein particles of the anti-infective agent are dispersed throughout the polymer.

21. The article of footwear of claim 16, wherein the metallic material comprises copper, a copper alloy, a coordinated copper complex, a copper-containing compound, or a copper chelate.

\* \* \* \* \*